(12) United States Patent
Laue et al.

(10) Patent No.: US 6,759,559 B2
(45) Date of Patent: *Jul. 6, 2004

(54) USE OF MOLECULAR WEIGHT-ENLARGED CATALYSTS IN A PROCESS FOR ASYMMETRIC, CONTINOUS HYDROGENATION, NOVEL MOLECULAR WEIGHT-ENLARGED LIGANDS AND CATALYSTS

(75) Inventors: Stephan Laue, Koenigswinter (DE); Andreas Liese, Juelich (DE); Christian Wandrey, Juelich (DE); Olaf Burkhardt, Kalmthout (DE); Jens Woeltinger, Hanau (DE); Andreas Bommarius, Atlanta, GA (US); Hans Henniges, Bonn (DE); Jean-Louis Philippe, Dreieich (DE); Andreas Karau, Neustad (DE); Karlheinz Drauz, Freigericht (DE)

(73) Assignees: Degussa AG, Duesseldorf (DE); Forschungszentrum Juelich GmbH, Juelich (DE)

( * ) Notice: Subject to any disclaimer, the term of this patent is extended or adjusted under 35 U.S.C. 154(b) by 202 days.

This patent is subject to a terminal disclaimer.

(21) Appl. No.: 09/767,879

(22) Filed: Jan. 24, 2001

(65) Prior Publication Data

US 2002/0016513 A1 Feb. 7, 2002

(30) Foreign Application Priority Data

Jan. 24, 2000 (DE) .......................... 100 02 975

(51) Int. Cl.$^7$ .............................. C07C 27/00

(52) U.S. Cl. .................. 568/814; 568/862; 502/158

(58) Field of Search .......................... 568/814

(56) References Cited

U.S. PATENT DOCUMENTS

| | | | |
|---|---|---|---|
| 5,200,335 A | * | 4/1993 | Hummel |
| 5,777,062 A | | 7/1998 | Pugin |
| 6,180,837 B1 | * | 1/2001 | Giffels |
| 6,403,522 B1 | * | 6/2002 | Bolm |
| 2001/0034417 A1 | * | 10/2001 | Burkhardt |
| 2002/0062004 A1 | * | 5/2002 | Krimmer |

FOREIGN PATENT DOCUMENTS

| | | | |
|---|---|---|---|
| DE | 10003110 | * | 9/2000 |
| DE | 100 03 110 | | 9/2000 |
| EP | 0 729 969 | | 9/1996 |
| EP | 0 877 029 | | 11/1998 |
| EP | 1048350 | * | 11/2000 |
| WO | WO 98/22415 | | 5/1998 |
| WO | WO 00/53305 | | 9/2000 |

OTHER PUBLICATIONS

Dennis J. Gravert et al, "Soluble Supports Tailored for Organic Synthesis: Parallel Polymer Synthesis via Sequential Normal/Living Free Radical Processes", J. Am. Chem. Soc., 1998, 120, pp. 9481–9495.

Eberhard Steckhan et al, "Kontinuierliche Erzeugung von NADH aus NAD⊕ und Formiat mit einem molekulargewichtsvergoesserten Homogenkatalysator in einem Membranreaktor", Angew. Chem., 1990, 102, Nr. 4, pp. 445–447.

Manfred T. Reetz et al, "Synthese und katalytische Wirkung von dendritischen Diposphan–Metallkomplexen", Angew. Chem., 1997, 109, Nr. 13/14, pp. 1559–1562.

Dieter Seebach et al, "Polymer– and Dendrimer–Bound Ti–TADDOLates in Catalytic (and Stoichiometric Enantioselective Reactions: Are Pentacoordinate Cationic Ti Complexes the Catalytically Active Species?", Helvetica Chimica Acta, 1996, vol. 79, pp. 1710–1740.

Udo Kragl et al, "Kontinuierliche asymmetrische Synthese in einem Membranreaktor", Angew. Chem., 1996, 108, Nr. 6, pp. 684–685.

Fritz Keller et al, "Chiral Polysiloxane–Fixed Metal 1,3–Diketonates (Chirasil–Metals) as Catalytic Lewis Acids for a Hetero Diels–Alder Reaction–Inversion of Enantioselectivity Upon Catalyst–Polymer Binding", Chem. Ber./Recueil, 1997, 130, pp. 879–885.

Carsten Bolm et al, "Asymmetrische Dihydroxylierung mit Polyethylenglycolmonomethylether–gebundenen Liganden", Angew. Chem. 1997, 109, Nr. 7, pp. 773–775.

Carsten Bolm et al, "Polymer–Supported Catalytic Asymmetric Sharpless Dihydroxylations of Olefins", Eur. J. Org. Chem, 1998, pp. 21–27.

Alessandro Mandoli et al, "A first example of macromolecular Ti(IV) Lewis acid in the catalytic enantioselective Mukaiyama reaction", Tetrahedron: Asymmetry, 1998, 9, pp. 1479–1482.

(List continued on next page.)

Primary Examiner—Michael L. Shippen
(74) Attorney, Agent, or Firm—Oblon, Spivak, McClelland, Maier & Neustadt, P.C.

(57) ABSTRACT

The first embodiment of the present invention provides a process, which includes:
   in a continuous process in a membrane reactor, asymmetrically hydrogenating at least one C═C, C═N or C═O double bond with a catalyst. Another embodiment of the present invention provides a ligand, which includes at least one di-1,3-aminophosphine homochiral active center; optionally, a linker; and a molecular weight-enlarging polymer; wherein the active center is bound to the molecular weight-enlarging polymer through the linker or is bound directly to the molecular weight-enlarging polymer; and wherein the linker is defined in the claims. Another embodiment of the present invention provides a process for preparing the above-noted ligand, and a catalyst that includes the above-noted ligand.

16 Claims, 3 Drawing Sheets

OTHER PUBLICATIONS

Juliane Beliczey et al, "Novel ligands derived from S-tyrosine for the enantioselective addition of diethylzinc to aldehydes", Tetrahedron: Asymmetry, 1997, vol. 8, No. 10, pp. 1529–1530.

Marcel Felder et al, "A polymer–enlarged homogeneously soluble oxazaborolidine catalyst for the asymmetric reduction of ketones by borane", Tetrahedron: Asymmetry, 1997, vol. 8, No. 12, pp. 1975–1977.

Christoph Koellner et al, "Dendrimers Containing Chrial Ferrocenyl Diphosphine Ligands for Asymmetric Catalysis", J. Am. Chem. Soc., 1998, 120, pp. 10274–10275.

Filippo Minutolo et al, "Polymer–Bound Chiral(Salen)Mn-(lll) Complex as Heterogeneous Catalyst in Rapid and Clean Enantioselective Epoxidation of Unfunctionalised Olefins", Tetrahedron Letters, 1996, vol. 37, No. 19, pp. 3375–3378.

Torsten Malmstroem et al, "A novel chiral water–soluble phosphine ligand based on a water–soluble acrylic acid salt", Chem. Commun., 1996, pp. 1135–1136.

Dennis J. Gravert et al, "Organic Synthesis on Soluble Polymer Supports: Liquid–Phase Methodologies", Chem. Rev., 1997, 97, pp. 489–509.

K.E. Geckler et al, "Soluble Polymer Supports for Liquid-Phase Synthesis", Advances in Polymer Science, 1995, vol. 121, pp. 31–79.

Georg Hochwimmer et al, "6,6'–Bisfunctionalized 2,2'–bipyridines as metallo–supramolecular initiators for the living polymerization of oxazolines", Macromol. Rapid Commun., 19, 1998, pp. 309–318.

Stephen J. Shuttleworth et al, "Functionalised Polymers: Recent Developments and New Applications in Synthetic Organic Chemistry", Synthesis, pp. 1217–1239.

Iwao Ojima , "The Chemistry of Organic Silicon Compounds", 1989, pp. 1479–1526.

Sebastian Rissom et al, "Asymmetric reduction of actophenone in membrane reactors: comparision of oxazaborolidine and alcohol dehydrogenase catalysed processes", Tetrahedron: Assymmetry, 1999, 10, pp. 923–928.

Matthew J. Palmer et al, "Asymmetric transfer hydrogenation of C=O and C=N bonds", Tetrahedron: Asymmetry, 10, 1999, pp. 2045–2061.

Ryoji Noyori et al, "Asymmetric Transfer Hydrogenation Catalyzed by Chiral Ruthenium Complexes", Acc. Chem. Res., 1997, 30, pp. 97–102.

Ryoji Noyori, "Asymmetric catalysis in organic synthesis", 1994, pp. 122–254.

Udo Kragl et al, "Applied Homogeneous Catalysis with Organometallic Compounds", 1996, pp 832–840, 842, 843.

Hidemasa Takaya et al, "Catalytic Asymmetric Synthesis", 1993, pp. 1–39.

Ulrich Nagel et al, "The enantioselective hydrogenation of N–acyl dehydroamino acids", Topics in Catalysis 5, 1998, pp. 3–23.

G. Bell et al, "Engineering Processes for Bioseperations", 1994, pp. 135–165.

C. W. Harwig, et al., Chemtracts–Organic Chemistry, vol. 12, pp. 1–26, "Soluble Polymers: New Options in Both Traditional and Combinatorial Synthesis", Jan. 1999.

U. Kragl, et al., Verfahrenstechnik Und Chemieingenieurwesen, pp. 151–166, "Membranreaktoren in der Organischen Synthese", 1998.

U. Nagel, et al., Chem. Ber., vol. 119, pp. 3326–3343, "Synthese N–Substituierter (R,R)–3,4–Bis(Diphenylphosphino)–Pyrrolidine Und Anwendung Ihrer Rhodiumkomplexe Zur Asymmetrischen Hydrierung Von α–(Acylamino)Acrylsaeure–Derivaten", 1986.

Transfer hydrogenations, Gladiali, Serafino; Mestroni, Giovanni. Germany, Editor(s): Beller, Matthias; Bolm, Carsten. Transitions Metals for Organic Synthesis (1998), 2.97–19. Publisher: Wiley–VCH Verlag GmbH, Weinheim, Germany CODEN: 66TUAZ Conference; General Review; CAN 129:315772 AN.

* cited by examiner

US 6,759,559 B2

USE OF MOLECULAR WEIGHT-ENLARGED CATALYSTS IN A PROCESS FOR ASYMMETRIC, CONTINOUS HYDROGENATION, NOVEL MOLECULAR WEIGHT-ENLARGED LIGANDS AND CATALYSTS

BACKGROUND OF THE INVENTION

1. Field of the Invention

The present invention relates to use of molecular weight-enlarged ligands and catalysts in a process for the asymmetric, continuous catalytic hydrogenation of C=C, C=N or C=O double bonds. This process is particularly suitable for continuous processes performed in a "membrane" reactor. The present invention also relates to molecular weight-enlarged catalysts and processes of making same.

2. Discussion of the Background

Continuous processes are highly preferred at the large industrial scale. In order to save on process costs, catalytically based processes are becoming more widely used in industry. Continuous catalytic processes are difficult to carry out because of the associated problems such as, for example, separability of the product from the catalyst, inactivation of the catalyst over time, and the development of suitable catalysts.

Recent attempts to overcome the above-mentioned problems include the separation of molecular weight-enlarged, homogeneously soluble catalysts from low molecular weight products by nano- and ultrafiltration membranes. Molecular weight-enlarged catalysts for homogeneous enantioselective hydrogenation are described, for example, in U.S. Pat. No. 5,777,062, which also describes the separation thereof from the reaction mixture. No mention is made of a continuously operated process, however.

J. Am. Chem. Soc. 1998, 120, 9481 et seq. addresses the problem of producing soluble molecular weight enlargements, inter alia, for hydrogenation catalysts. Wandrey et al have also reported the use of a molecular weight-enlarged hydrogenation catalyst in a membrane reactor (Angew. Chem. (1990), 102, 445 et seq.). In this case, the desired substrate, $NAD^+$, is symmetrically hydrogenated by the catalyst. Only thereafter does the asymmetric hydrogen transfer occur with the assistance of an alcohol dehydrogenase on the C=O bond.

Hydrogenation processes proposed to date in the conventional processes operate discontinuously and/or require a mediator such as alcohol dehydrogenase. Thus, the above-described problems and others have not been adequately solved to date, and there is still a need for novel catalyst systems which make it possible to perform continuous processes catalytically.

SUMMARY OF THE INVENTION

Accordingly, one object of the present invention is to provide a continuously operating catalytic, asymmetric hydrogenation process.

Another object of the present invention is to provide a continuously operating catalytic and asymmetric hydrogenation process using molecular weight-enlarged catalysts.

Another object of the present invention is to provide a continuously operating catalytic and asymmetric hydrogenation process in which the product is easily separated from the reaction mixture.

Another object of the present invention is to provide a molecular weight-enlarged ligand for preparing such a catalyst.

Another object of the present invention is to provide a method for preparing such ligands and catalysts.

Another object of the present invention is to provide a homogeneous soluble hydrogenation catalyst that is readily separable from the hydrogenation product.

These and other objects have been achieved by the present invention, the first embodiment of which provides a process, which includes:

in a continuous process in a membrane reactor, asymmetrically hydrogenating at least one C=C, C=N or C=O double bond with a molecular weight-enlarged catalyst.

Another embodiment of the present invention provides a ligand, which includes:

at least one di-1,3-aminophosphine homochiral active center;

optionally, a linker; and a molecular weight-enlarging polymer;

wherein the active center is bound to the molecular weight-enlarging polymer through the linker or is bound directly to the molecular weight-enlarging polymer; and wherein the linker is a member selected from the group including formulae (a)–(g):

| | | |
|---|---|---|
| a) | $-Si(R_2)-$ | |
| b) | $-(SiR_2-O)_n-$ | n = 1–10000 |
| c) | $-(CHR-CHR-O)_n-$ | n = 1–10000 |
| d) | $-(X)_n-$ | n = 1–20 |
| e) | $Z-(X)_n-$ | n = 0–20 |
| f) | $-(X)_n-W$ | n = 0–20 |
| g) | $Z-(X)_n-W$ | n = 0–20 | wherein

R is H, $(C_1-C_8)$ alkyl, $(C_6-C_{18})$ aryl, $(C_7-C_{19})$ aralkyl, or $((C_1-C_8)$ alkyl$)_{1-3}-(C_6-C_{18})$ aryl;

X is $(C_6-C_{18})$ arylene, $(C_1-C_8)$ alkylene, $(C_1-C_8)$ alkenylene, $((C_1-C_8)$ alkyl$)_{1-3}-(C_6-C_{18})$ arylene, or $(C_7-C_{19})$ aralkylene;

Z is C(=O)O—, C(=O)NH—, C(=O)—, NR, O, CHR, $CH_2$, C=S, S, or PR; Z being bound directly to the molecular weight-enlarging polymer; and W is C(=O)O—, C(=O)NH—, C(=O)—, NR, O, CHR, $CH_2$, C=S, S, PR, W being bound directly to the active center.

Another embodiment of the present invention provides a process for preparing the above-noted ligand, which includes at least one step selected from the group including (a)–(c):

(a) binding the active center to a monomer directly or through a linker to provide a modified monomer, and polymerizing the modified monomer in the presence of one or more unmodified monomers;

(b) binding the active center to a polymer, either directly or through linker; and (c) carrying out either of steps (a) or (b), and further polymerizing the resulting polymer with one or more additional polymers, wherein the one or more additional polymers optionally include one or more catalytically active centers.

Another embodiment of the invention provides a catalyst, that includes the above-noted ligand and one or more metals or metal ions selected from the group including Ru, Rh, Ir, Pd, Ni, Pt, Co, ions thereof, and mixtures thereof.

DESCRIPTION OF THE PREFERRED EMBODIMENTS

Figure 1:
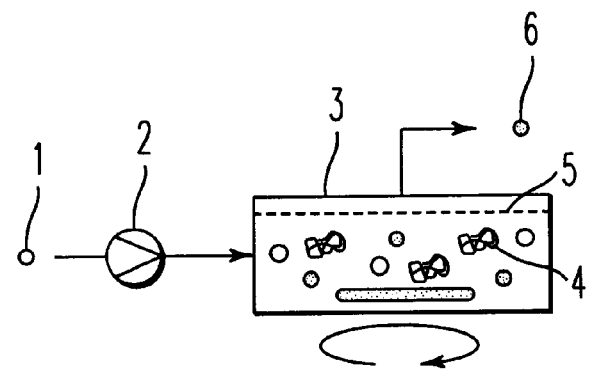
FIG. 1 shows a membrane reactor with dead end filtration. The substrate 1 is transferred by means of a pump 2 into the reaction chamber 3, which includes a membrane 5. In addition to the solvent, the stirred reaction chamber contains the catalyst 4, the product 6 and unreacted substrate 1. Low molecular weight 6 is primarily filtered out through the membrane 5.

Various other objects, features and attendant advantages of the present invention will be more fully appreciated as the same becomes better understood from the following detailed description when considered in connection with the accompanying drawings in which like reference characters designate like or corresponding parts throughout the several views.

Preferably, by using molecular weight-enlarged, homogeneously soluble catalysts in a membrane reactor for the asymmetric, continuous hydrogenation of C=C, C=N or C=O double bonds, wherein the asymmetric transfer of the hydrogen onto the substrate to be hydrogenated is effected by the catalyst, the objects of the invention are achieved in a surprising and advantageous manner.

The hydrogenation (asymmetric transfer of hydrogen to or across the double bond) is carried out by the catalyst, without the need for a mediator such as alcohol dehydrogenase. Most preferably, the asymmetric transfer is carried out in the substantial absence or complete absence of a mediator such as alcohol dehydrogenase.

Figure 2:
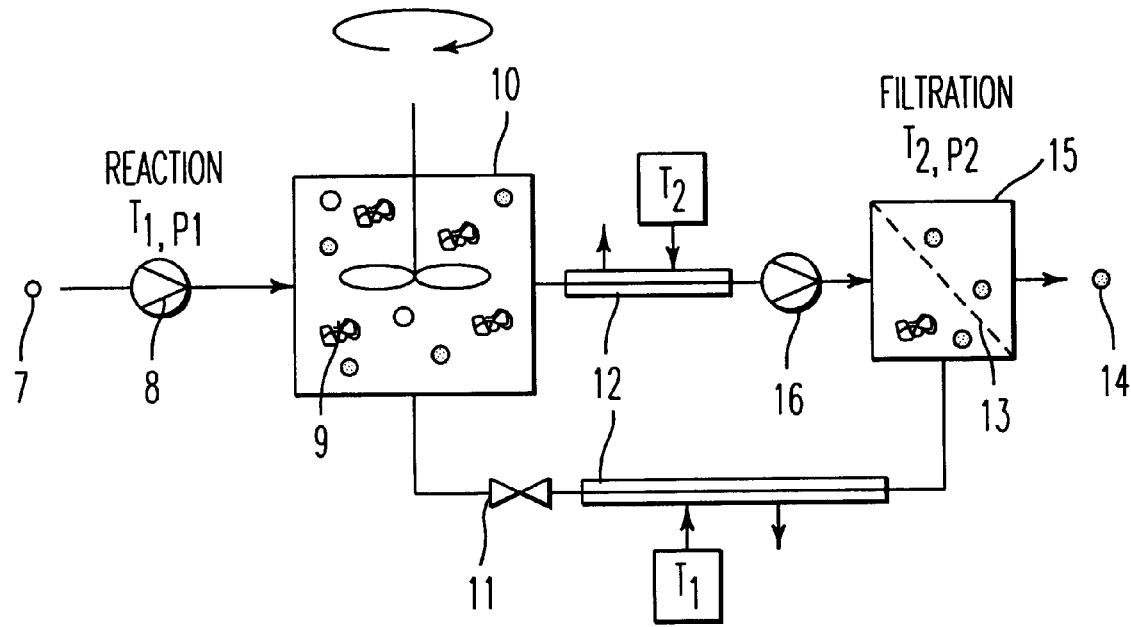
FIG. 2 shows a membrane reactor with crossflow filtration. In this case, the substrate 7 is transferred by means of the pump 8 into the stirred reaction chamber, which also contains solvent, catalyst 9 and product 14. A stream of solvent is established by means of the pump 16, which stream passes via an optionally present heat exchanger 12 into the crossflow filtration cell 15. It is here that the low molecular weight product 14 is separated by means of the membrane 13. High molecular weight catalyst 9 is then passed with the solvent stream optionally through the valve 11, optionally again through a heat exchanger 12, back to the reactor 10.

Continuous operation may be performed as desired using the crossflow filtration mode (FIG. 2) or as dead end filtration (FIG. 1).

In the case of dead end operation, catalyst and solvent are initially introduced into the reactor and the dissolved substrate is then apportioned, wherein a source of hydrogen must simultaneously be present. The substrate is enantioselectively reduced by means of the catalyst and then discharged from the membrane reactor with the solvent stream via the filtration membrane.

In the case of crossflow operation, the reaction solution containing solvent, substrate, product and catalyst as well as a hydrogen source, is passed in front of a membrane, across which a pressure differential prevails.

In both cases, the dissolved substrate is apportioned at such a rate that the permeated solution predominantly contains enantioselectively hydrogenated product. Both process variants have been described in the literature (Engineering Processes for Bioseparations, ed.: L. R. Weatherley, Heinemann, 1994, 135–165, the relevant contents of which are hereby incorporated by reference).

The substrate for asymmetric hydrogenation is not particularly limited, so long as it contains one or more C=C, C=N or C=O double bonds. Mixtures are possible.

The hydrogen source for the hydrogenation according to the invention may be gaseous hydrogen which is introduced into the system during the reaction. In this case, the entire apparatus is preferably located in a hydrogen atmosphere at hydrogenation pressure, such that the same hydrogen pressure prevails on both sides of the filtration membrane and hydrogen thus cannot diffuse out of the system via the filtration membrane. This would entail considerable loss of hydrogen.

In addition, the reaction pressure conditions across the membrane may consequently more readily be adjusted as mentioned above. An elevated pressure differential before and after the membrane would result in outgassing on the filtrate side, which could result in equipment problems. Moreover, increased passage of hydrogen through the membrane could accelerate fouling.

This method is preferably performed at hydrogen pressures of 0.1–100, preferably of 0.2–0.5 MPa, which ranges include all values and subranges therebetween, including 0.75, 1, 3, 4, 6, 8, 9, 11, 12, 14, 15, 17, and 19 MPa.

In another preferred development, hydrogenation is performed by the transfer hydrogenation method. This method is described, for example, in the literature ("Asymmetric transfer hydrogenation of C=O and C=N bonds", M. Wills et al. Tetrahedron: Asymmetry 1999, 10, 2045; "Asymmetric transfer hydrogenation catalysed by chiral ruthenium complexes", R. Noyori et al. Acc. Chem. Res. 1997, 30, 97; "Asymmetric catalysis in organic synthesis", R. Noyori, John Wiley & Sons, New York, 1994, p.123; "Transition metals for organic Synthesis", eds. M. Beller, C. Bolm, Wiley-VCH, Weinheim, 1998, vol. 2, p. 97; "Comprehensive Asymmetric Catalysis", eds.: Jacobsen, E. N.; Pfaltz, A.; Yamamoto, H., Springer-Verlag, 1999, the relevant contents of each of which are hereby incorporated by reference).

Preferred hydrogen-producing sources used in this case include alcohols, formates, cyclohexene or cyclohexadiene, very particularly preferably isopropyl alcohol, in the presence of a base.

In the case of transfer hydrogenation using the isopropylate system, it has proved convenient to ensure optimal apportionment of base for the continuous operation.

Figure 3:
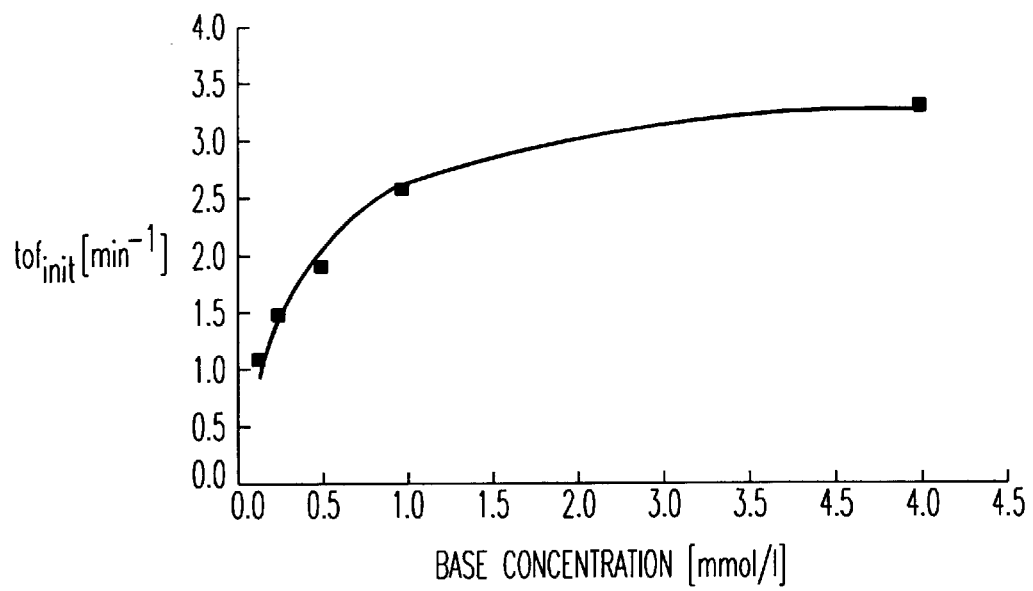
FIGS. 3–6 depict various data obtained in the Examples section.

Preferably, in order to elevate catalytic activity, a base, preferably isopropylate, should be present in the reaction mixture. It has been found that elevated base concentrations bring about elevated catalytic activity. FIG. 3 shows the influence of base concentration on turn-over frequency (TOF).

Without wishing to be bound by theory, the base is believed to accelerate the production of an activated species of catalyst and/or accelerate the production of hydrogen. This effect is believed to be distinct from the effect of a mediator. Indeed, the catalytic asymmetric transfer reaction surprisingly and unexpectedly proceeds without any need for a mediator; and the addition of a base is preferred only as a way to elevate catalytic activity.

Figure 4:
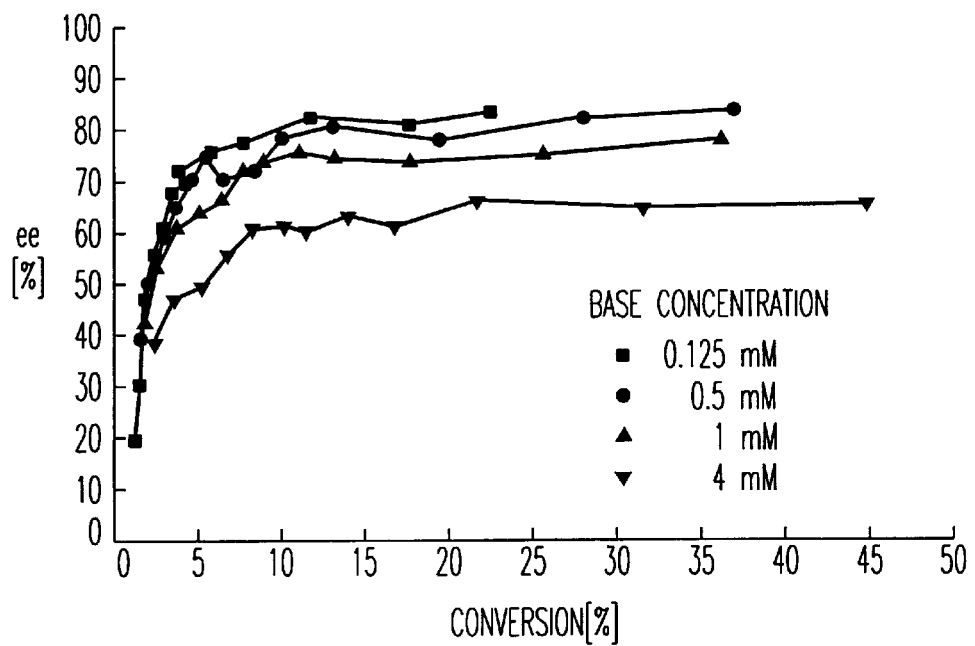

In the present catalyst system, elevated base concentrations are unexpectedly observed to have a negative effect on the achievable enantiomeric excess. FIG. 4 shows the influence of base concentration on ee value in the reduction of acetophenone.

This effect has not previously been described in the literature. With a view to achieving maximum enantiomeric excesses, it is thus preferable to find a compromise between adequate catalytic activity and the highest possible enantioselectivity. This applies in particular in the case of continuous performance of the reaction.

Figure 5:
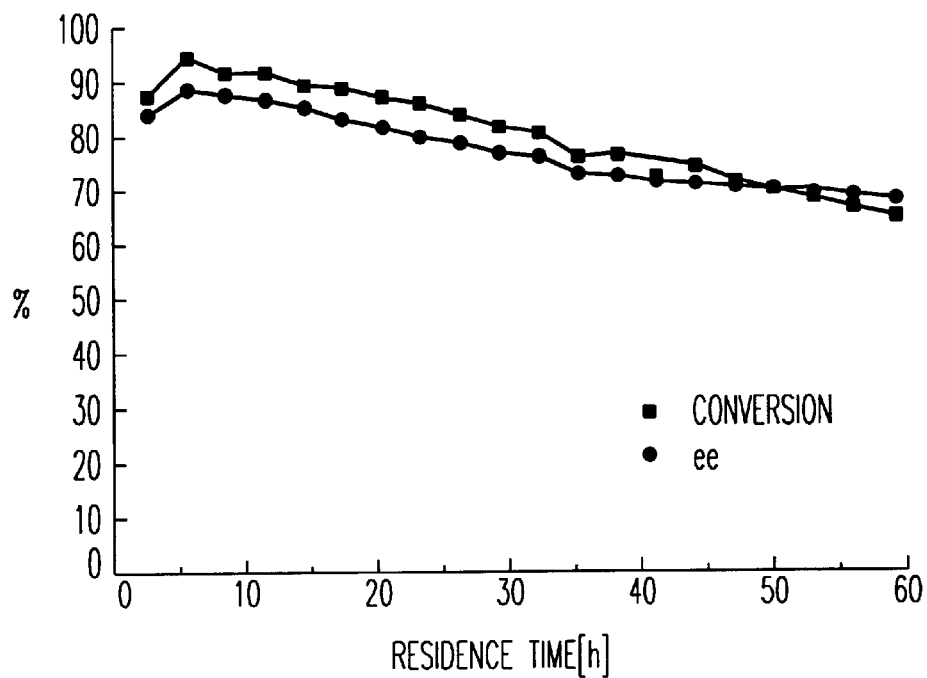

In FIG. 5, it is seen that, while apportioning a large quantity of base at once (5 equivalents of base relative to the catalyst) does indeed bring about adequate activation of the catalyst at the beginning of the test, both enantiomeric excess and conversion constantly subside over the course of the test. The constant decrease in conversion in this case is believed to occur by a reversible deactivation of the catalyst by moisture and by flushing of the base out of the reactor. Furthermore, flushing out of the base, which is possibly associated with the catalyst (as a kind of co-factor), also brings about a reduction in conversion.

Figure 6:
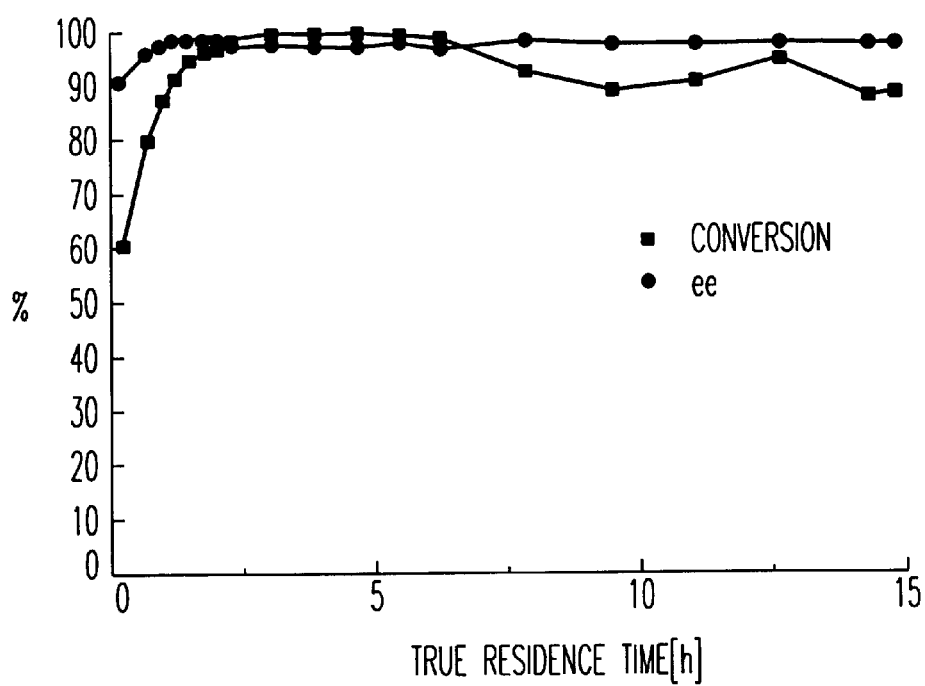

Preferably, the catalyst is activated once with a small quantity of base (0.5–1.5 equivalents) and then constantly to apportion a small quantity of base to offset the above-stated effects in order to ensure optimum progress of the process (FIG. 6). More preferably, the quantity of base is 0.6 to 1.4, more particularly preferably 0.7 to 1.3, more especially preferably 0.8 to 1.2, and most preferably 0.9 to 1.1, which ranges include all values and subranges therebetween.

The molecular weight-enlarged, homogeneously soluble hydrogenation catalyst may be synthesized from molecular weight enlargement (polymer), optionally linker and active center.

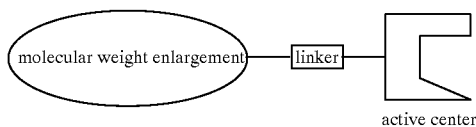

Molecular Weight Enlargement:

For the purposes of the invention, the molecular weight enlargement may be freely selected. The enlargement is limited, on the one hand, by considerations of practicability and cost and, on the other, by technical issues (retention capacity, solubility etc.). Especially preferable polymer enlargements for catalysts are described in Reetz et al., Angew. Chem. 1997, 109, 1559 et seq.; Seebach et al., Helv. Chim Acta 1996, 79, 1710 et seq.; Kragl et al., Angew. Chem. 1996, 108, 684 et seq.; Schurig et al., Chem. Ber./Recueil 1997, 130, 879 et seq.; Bolm et al., Angew. Chem. 1997, 109, 773 et seq.; Bolm et al. Eur. S. Org. Chem. 1998, 21 et seq.; Baystone et al. in Speciality Chemicals 224 et seq.; Salvadori et al., Tetrahedron: Asyrnmetry 1998, 9, 1479; Wandrey et al., Tetrahedron: Asymmetry 1997, 8, 1529 et seq.; ibid. 1997, 8, 1975 et seq.; Togni et al. J. Am. Chem. Soc. 1998, 120, 10274 et seq., Salvadori et al., Tetrahedron Lett. 1996, 37, 3375 et seq.; WO 98/22415; in particular DE 19910691.6; Janda et al., J. Am. Chem. Soc. 1998, 120, 9481 et seq.; Andersson et al., Chem. Commun. 1996, 1135 et seq.; Janda et al., Soluble Polymers 1999, 1, 1; Janda et al., Chem. Rev. 1997, 97, 489; Geckler et al., Adv. Polym. Sci. 1995, 121, 31; White et al., in "The Chemistry of Organic Silicon Compounds", Wiley, Chichester, 1989, 1289; Schuberth et al., Macromol. Rapid Commun. 1998, 19, 309; Sharma et al., Synthesis 1997, 1217; "Functional Polymers" ed.: R. Arshady, ASC, Washington, 1996; "Praktikum der Makromolekularen Stoffe", D. Braun et al., VCH-Wiley, Weinheim 1999, the relevant contents of each of which are hereby incorporated by reference).

Preferred molecular weight-enlarging polymers for binding the ligands are polyacrylates, polyvinylpyrrolidinones, polysiloxanes, polybutadienes, polyisoprenes, polyalkanes, polystyrenes, polyoxazolines or polyethers (PEG, PEP) or mixtures thereof. Preferably, mixtures are taken to mean the fact that individual polymers of differing origin are polymerized together to yield block polymers. Random mixtures of monomers in the polymer are also possible.

Polyacrylates, polysiloxanes, polystyrenes and/or polyethers are very particularly preferred for this purpose.

The molecular weight-enlarging polymers may exhibit an average molecular weight in the range from 1,000–1,000,000, preferably from 5,000–500,000, particularly preferably from 5,000–300,000 g/mol, which ranges include all values and subranges therebetween.

Linkers:

A linker may be inserted between the actual catalyst or ligand (active center) and the polymer enlargement. The catalyst may, however, also be bound directly to the polymer enlargement.

The purpose of the linker is to provide a space between the active center and polymer in order to mitigate or eliminate any mutual interactions which are disadvantageous to the reaction.

Linkers may, in principle, be freely selected by the person skilled in the art. Selection should be made on the basis of how readily they may be coupled, on the one hand, to the polymer/monomer and, on the other, to the active center. Suitable linkers may be found inter alia in the literature references mentioned above in relation to the molecular weight enlargement.

For the purposes of the invention, these actual active hydrogenation catalysts (active centers) are accordingly bound to the polymer enlargement directly or preferably via a linker selected from the group

| a) | —Si(R$_2$)— | |
| b) | —(SiR$_2$—O)$_n$— | n = 1–10000 |
| c) | —(CHR—CHR—O)$_n$— | n = 1–10000 |
| d) | —(X)$_n$— | n = 1–20 |
| e) | Z—(X)$_n$— | n = 0–20 |
| f) | —(X)$_n$—W | n = 0–20 |
| g) | Z—(X)$_n$—W | n = 0–20 | wherein

R means H, ($C_1$–$C_8$) alkyl, ($C_6$–$C_{18}$) aryl, ($C_7$–$C_{19}$) aralkyl, (($C_1$–$C_8$) alkyl)$_{1,3}$($C_6$–$C_{18}$) aryl, X means ($C_6$–$C_{18}$) arylene, ($C_1$–$C_8$) alkylene, ($C_1$–$C_8$) alkenylene, (($C_1$–$C_8$) alkyl)$_{1-3}$—($C_6$–$C_{18}$) arylene, ($C_7$–$C_{19}$) aralkylene, Z means on the polymer side C(=O)O—, C(=O)NH—, C(=O)—, NR, O, CHR, CH$_2$, C=S, S, PR, W means on the ligand side C(=O)O—, C(=O)NH—, C(=O)—, NR, O, CHR, CH$_2$, C=S, S, PR.

Other preferred compounds which may be used as linkers are shown in the following scheme:

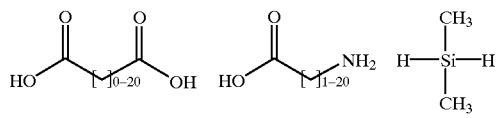

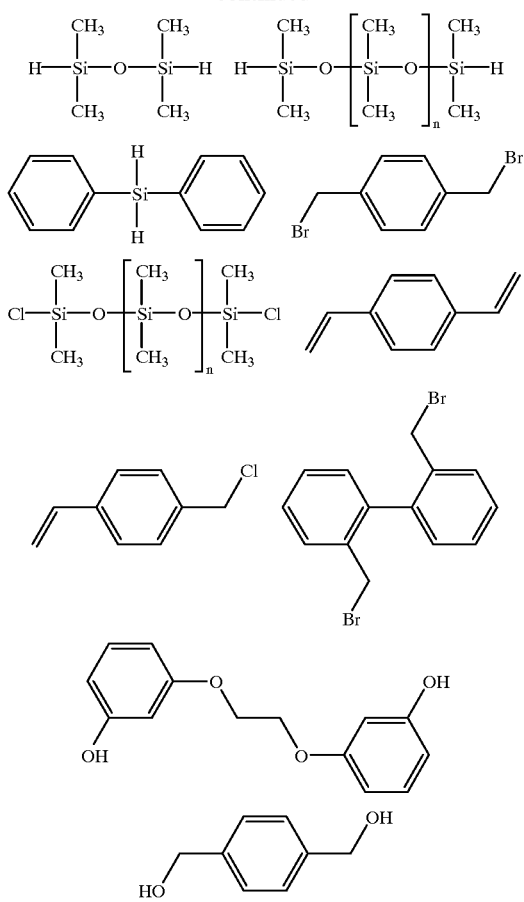

Very particularly preferred linkers, however, are those such as, for example, 1,4'-biphenyl, 1,2-ethylene, 1,3-propylene, PEG (2-10), α,ω-siloxanylene or 1,4-phenylene and α,ω-1,4-bisethylenebenzene or linkers which are obtainable from siloxanes of the general formula I:

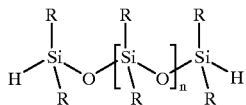

(I)

R: Me, Et
n = 0–10

These may readily be bound to any double bonds present in the polymers and suitable functional groups of the active centers under hydrosilylation conditions (review of the hydrosilylation reaction by Ojima in The Chemistry of Organic Silicon Compounds, 1989 John Wiley & Sons Ltd., 1480–1526, the relevant contents of which are hereby incorporated by reference).

Active Centers:

For the purposes of the invention, an active center (or homochiral active center) is taken to mean the actual low molecular weight ligand which has hitherto normally been used for the hydrogenation. As explained above, this may be attached to the molecular weight enlargement directly or via a linker as stated above.

Active centers which may be considered are, in principle, any ligands known to the person skilled in the art for asymmetric, catalytic hydrogenation. Especially preferable compounds may be found in:

"Asymmetric transfer hydrogenation of C=O and C=N bonds", M. Wills et al. Tetrahedron: Asymmetry 1999, 10, 2045;

"Asymmetric transfer hydrogenation catalysed by chiral ruthenium complexes" R. Noyori et al. Acc. Chem. Res. 1997, 30, 97;

"Asymmetric catalysis in organic synthesis", R. Noyori, John Wiley & Sons, New York, 1994, p.123;

"Transition metals for organic Synthesis" eds. M. Beller, C. Bolm, Wiley-VCH, Weinheim, 1998, vol. 2, p.97;

"Comprehensive Asymmetric Catalysis" eds.: Jacobsen, E. N.;

Pfaltz, A.; Yamamoto, H., Springer-Verlag, 1999; "Catalytic Asymmetric Synthesis", ed.: I. Ojima, Wiley-VCH, 1993, 1–39 and U.S. Pat. No. 5,777,062, the relevant contents of each of which are hereby incorporated by reference.

Particularly readily usable active centers are those which firstly ensure elevated optical yield combined with the fastest possible hydrogenation, so resulting in an elevated throughput. The active center should furthermore be sufficiently insensitive to oxidation by atmospheric oxygen such that it is not necessary to use degassed solvent and adequate storage stability of the ligands is provided.

The following may be considered to be very particularly advantageous active centers:

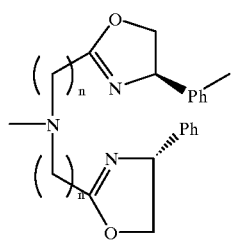

N = 0–5

-continued
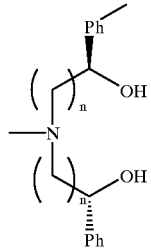
N = 0–5
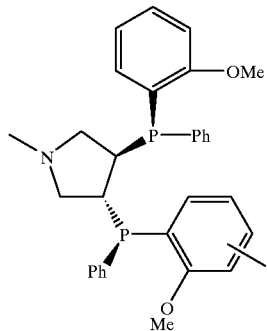
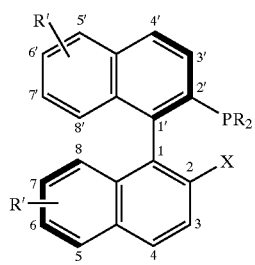
R = cyclohexyl, (C_6–C_18) aryl
R' = H, polymer linkage
X = PR_2, Ome
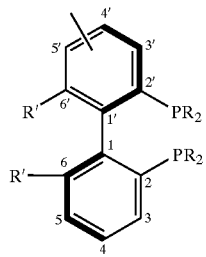
R = cyclohexyl, (C_6–C_18) aryl
R' = CH_3, OMe, CF_3, H, tert.$^t$Bu
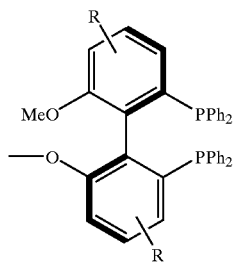
R = H, CF_3, OMe, CH_3
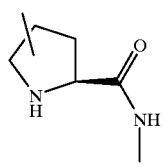

-continued
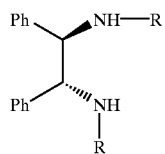
R = H, (C₁–C₈) alkyl or polymer linkage
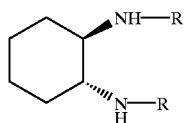
R = H, (C₁–C₈) alkyl or polymer linkage
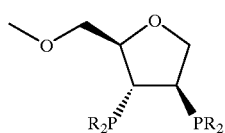
R = cyclohexyl, (C₆–C₁₈) aryl
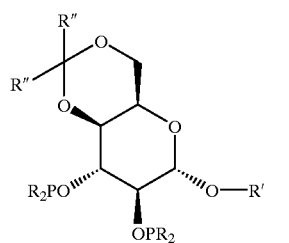
R = cyclohexyl, (C₆–C₁₈) aryl
R' = (C₁–C₈) alkyl, (C₇–C₁₉) aralkyl, (C₆–C₁₈) aryl, polymer linkage
R" = (C₁–C₈) alkyl or polymer linkage
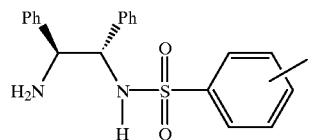
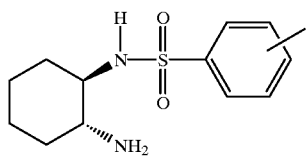
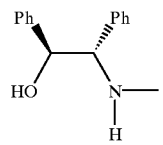
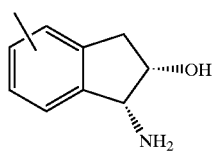

-continued

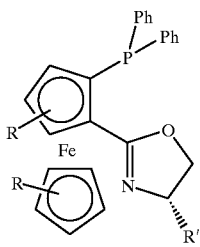

R' = H, polymer linkage
R' = (C$_1$–C$_8$) alkyl,
(C$_7$–C$_{19}$) aralkyl, (C$_6$–C$_{18}$) aryl

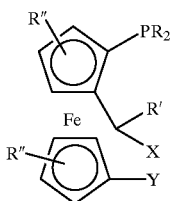

R = cyclohexyl, (C$_6$–C$_{18}$) aryl
R' = (C$_1$–C$_8$) alkyl, H, polymer linkage
R'' = H, polymer linkage
X = NR'$_2$, NR'H, OMe, Oac
Y = PR$_2$, H

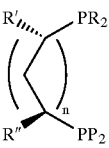

R = cyclohexyl, (C$_6$–C$_{18}$) aryl
R' = (C$_1$–C$_8$) alkyl, (C$_6$–C$_{18}$) aryl, H
R'' = polymer linkage
N = 0, 1, 2

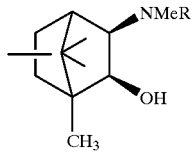

R = H, (C$_1$–C$_8$) alkyl, polymer linkage

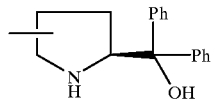

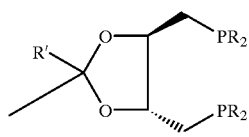

R = cyclohexyl, (C$_6$–C$_{18}$) aryl
R' = H, (C$_1$–C$_8$) alkyl, (C$_6$–C$_{18}$) aryl

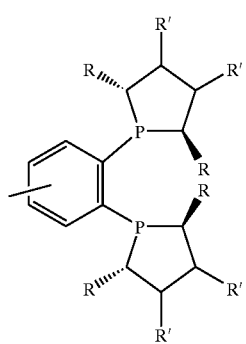

R = (C$_1$–C$_8$) alkyl
R' = H, O—(C$_1$–C$_8$) alkyl,
O—(C$_7$–C$_{19}$) aralkyl,
O—(C$_6$–C$_{18}$) aryl, OH

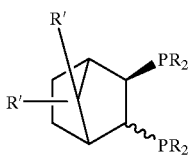

R = cyclohexyl, (C$_6$–C$_{18}$) aryl
R' = H, polymer linkage

-continued
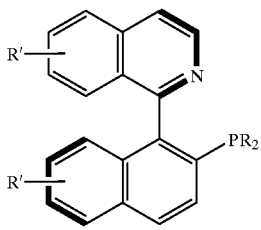
R = cyclohexyl, $(C_6-C_{18})$ aryl  
R' = H, polymer linkage
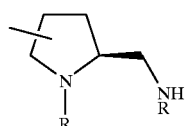
R = H, $(C_1-C_8)$ alkyl,  
$(C_7-C_{19})$ aralkyl, polymer linkage
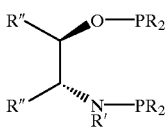
R = cyclohexyl, $(C_6-C_{18})$ aryl  
R' = H, $(C_1-C_8)$ alkyl,  
polymer linkage  
R" = H, $(C_1-C_8)$ alkyl,  
$(C_7-C_{19})$ aralkyl,  
$(C_6-C_{18})$ aryl, polymer linkage
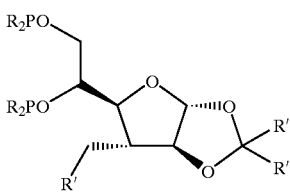
R = cyclohexyl, $(C_6-C_{18})$ aryl  
R' = H, $(C_1-C_8)$ alkyl, $(C_7-C_{19})$ aralkyl,  
$(C_6-C_{18})$ aryl, polymer linkage
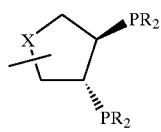
R = cyclohexyl, $(C_6-C_{18})$ aryl  
X = $CH_2$, O, S, PR
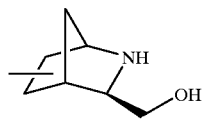
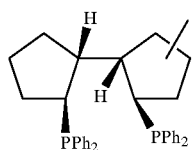
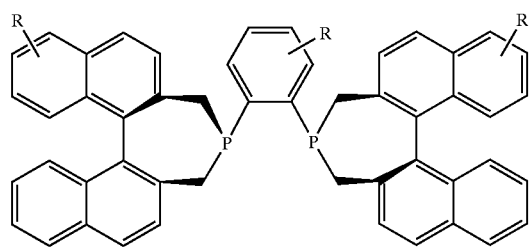
R = H, polymer linkage -continued
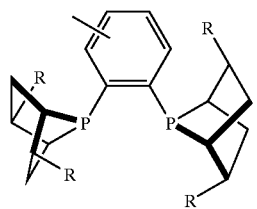
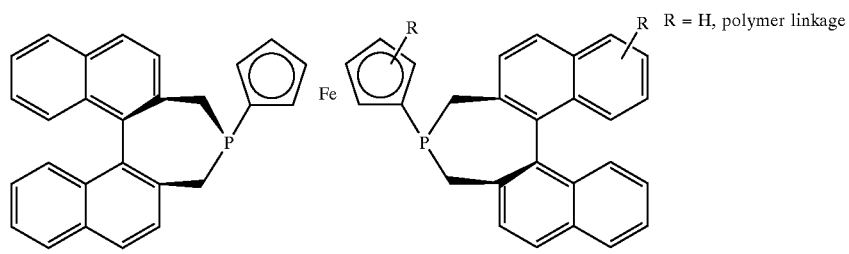
R = H, polymer linkage
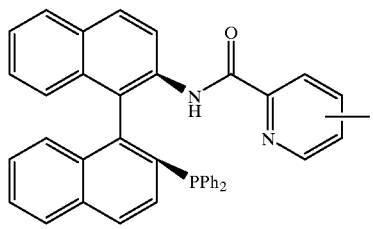
(n = 1–6)
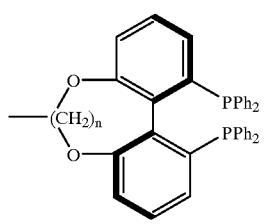
R = (C$_1$–C$_8$) alkyl, (C$_7$–C$_{19}$) aralkyl, (C$_6$–C$_{18}$) aryl, polymer linkage
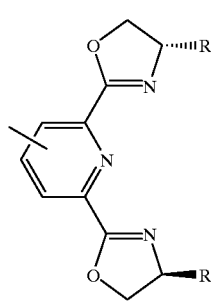

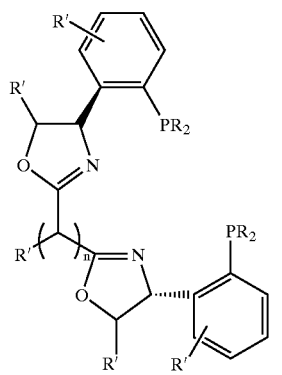
R = cyclohexyl, $(C_6-C_{18})$ aryl
R' = H, $(C_1-C_8)$ alkyl,
$(C_7-C_{19})$ aralkyl,
$(C_6-C_{18})$ aryl, polymer linkage
N = 0–5
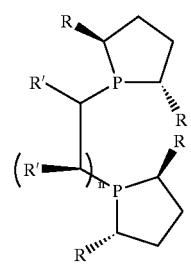
N = 0,1
R = $(C_1-C_8)$ alkyl, H
R' = H, $(C_1-C_8)$ alkyl,
$(C_7-C_{19})$ aralkyl,
$(C_6-C_{18})$ aryl, polymer linkage
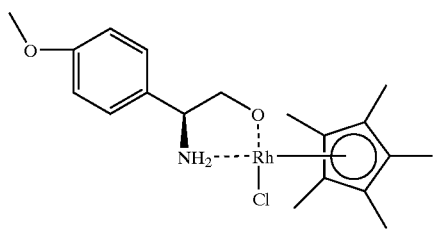
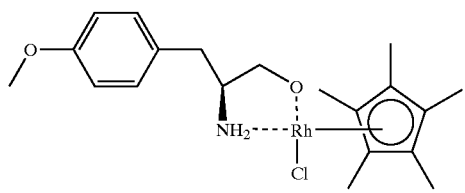
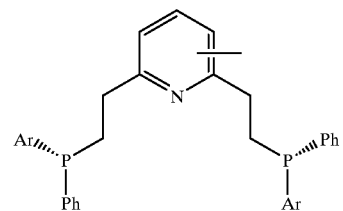
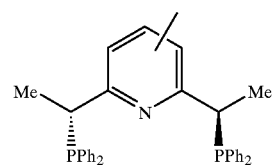

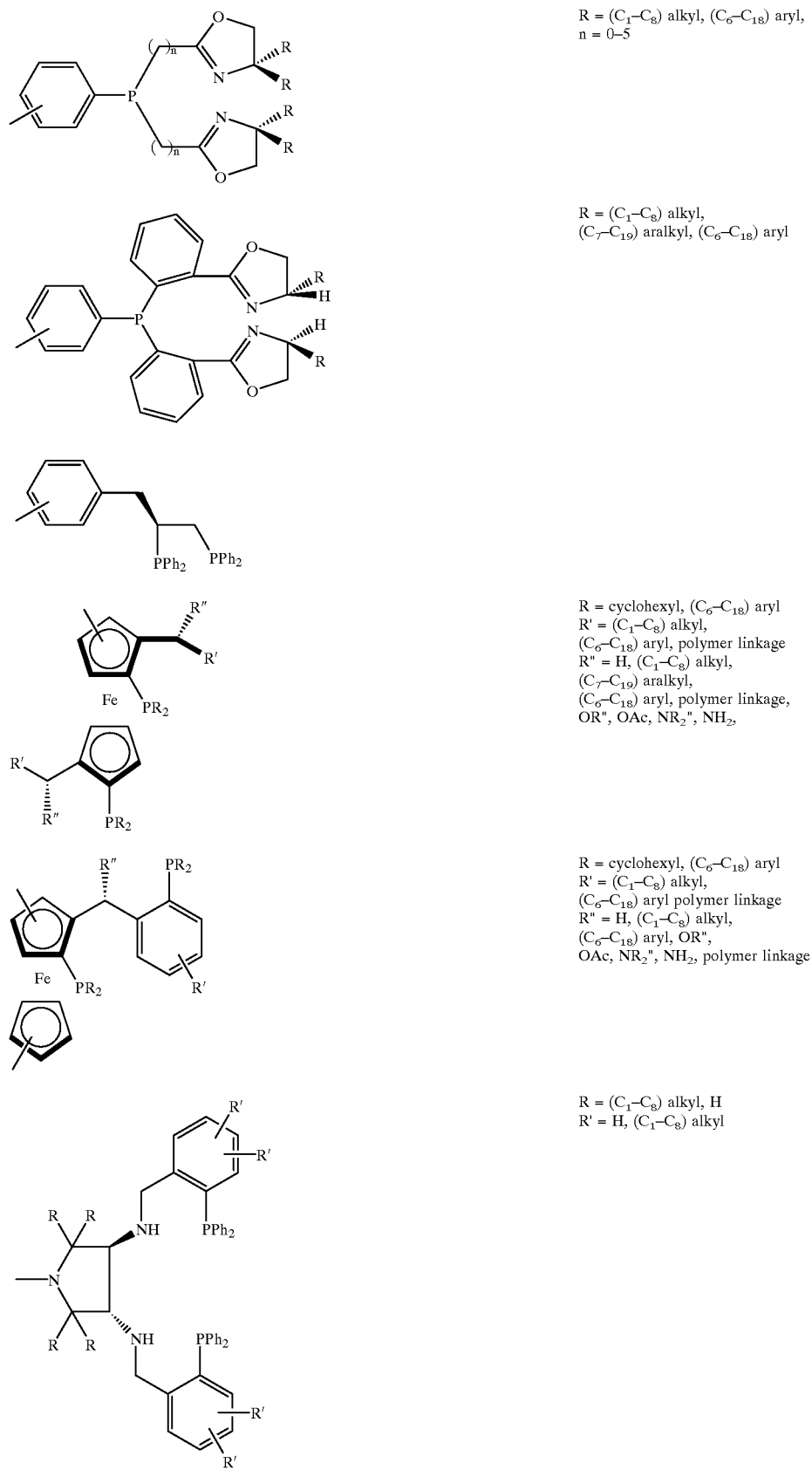

-continued

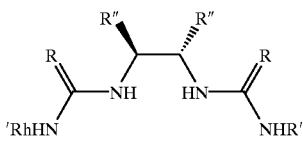

R = O, S, HH
R' = H, $(C_1-C_8)$ alkyl,
$(C_7-C_{19})$ aralkyl,
$(C_6-C_{18})$ aryl, polymer linkage
R" = $(C_1-C_8)$ alkyl,
$(C_7-C_{19})$ aralkyl, $(C_6-C_{18})$ aryl

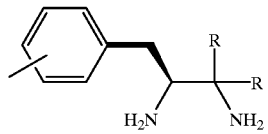

R = $(C_1-C_8)$ alkyl,
$(C_7-C_{19})$ aralkyl, $(C_6-C_{18})$ aryl,

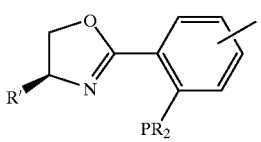

R = $(C_1-C_8)$ alkyl,
$(C_7-C_{19})$ aralkyl, $(C_6-C_{18})$ aryl
R" = $(C_1-C_8)$ alkyl,
$(C_7-C_{19})$ aralkyl, $(C_6-C_{18})$ aryl

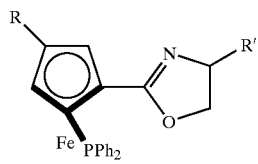

R = polymer linkage, H
R' $(C_1-C_8)$ alkyl, $(C_7-C_{19})$ aralkyl,
$(C_6-C_{18})$ aryl polymer linkage

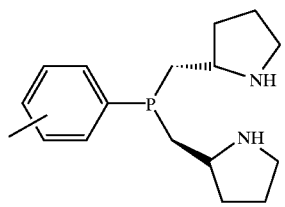

The indicated bonds in the chemical structures stated in the table are the preferred binding sites both for the polymer and for the optionally used linker. More preferably, one of the indicated possibilities for binding may be adequate. Even more preferably, the possibility of polymer linkage is stated for specific residues in the right hand column of the table. This should also be taken to apply to the possibility of binding the linkers.

In the above table showing the structures of the homochiral active centers (hereinafter also referred to as the "table"), the ranges of carbon numbers given for the respective R, R', and R" and in the accompanying description for the linker, each range of carbon numbers for the alkyl, aryl, aralkyl, alkylene, arylene, alkenylene, and aralkenylene includes all values and subranges therebetween, including $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$ and $C_{19}$.

Where heteroatoms are present in the active centers which are not involved in complexing the metal, the active centers are preferably bound via these atoms, such as for example in general structures 1–3 via the amino function.

In general structure 4, linkage in positions 5-7 or 5'-7' is particularly suitable, with position 6 or 6' being extremely preferred.

In general structure 5, position 4-6 or 4'-6' is highly suitable. Position 5 or 6 or 5' or 6' may particularly readily be selected.

The first five general structures in the above table are particularly preferable active centers.

Especially preferred active centers are di-1,3-aminophosphines, optionally of the following structure

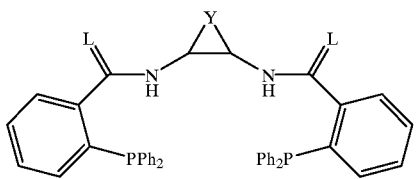

wherein Y may be a $(C_1-C_8)$ alkylene group, which may alternatively be maximally unsaturated or partially or entirely saturated, and/or may contain one or more heteroatoms, such as N, P, O, S; and L may be HH, O or S.

It is within the scope of the invention that, in accordance with the knowledge of a person skilled in the art, the above-stated constituents of the molecular weight-enlarged catalyst (molecular weight enlargement, linker, active center) may be combined at will with regard to optimizing the manner in which the reaction is performed.

Combining Molecular Weight Enlargement with Linker/Active Center:

Two preferable methods for attaching the linkers/active centers to the molecular weight enlargement include:

(a) the catalytically active center may be bound with a bound linker or directly to a monomer and the latter is polymerized in the presence of unmodified monomers, or (b) the catalytically active center is bound via a linker or directly to the molecular weight enlargement.

It is optionally possible to prepare polymers according to (a) or (b), which may be further copolymerized with other polymers, which include catalytically active centers and may be produced according to (a) or (b).

Preferably, the number of linkers/active centers per monomer in the polymer is such that as many catalytically active centers as possible should be located on a polymer, such that conversion per polymer is consequently increased. On the other hand, however, the centers should preferably be spaced apart in such a manner that any mutual negative influence on reactivity (TOF, selectivity) is minimized or does not occur. The spacing between linkers/active centers in the polymer should thus preferably be in the range from 1–200 monomer units, more preferably 5–25 monomer units, and most preferably 10 to 15 monomer units, which ranges include all values and subranges therebetween.

Preferably, the sites on the polymer or on the monomer to be polymerized which are used for binding the linker/active center are those which may readily be functionalized or permit an existing functionality to be used for binding. Heteroatoms or unsaturated carbon atoms are thus preferably suitable for binding the components.

For example, in the case of styrene/polystyrene, the aromatic rings which are present may be used as attachment points to the linkers/active centers. Functionalities may readily be linked to these aromatic rings, preferably in positions 3, 4, 5, particularly preferably in position 4, by means of standard aromatic chemistry. It is, however, also advantageous to incorporate a for example already functionalized monomer into the mixture to be polymerized and, after polymerization, to bind the linker to the functionalities present in the polystyrene. Compounds which are advantageously suitable for this purpose are, for example, para-hydroxy-, para-chloromethyl or para-aminostyrene derivatives.

the linker or the active center may be bound preferably via an ester or amide bond before or after polymerization.

Polysiloxanes as a molecular weight enlargement are preferably synthesized such that, in addition to dimethylsilane units, hydromethylsilane units are also present. The linkers/active centers may then furthermore be coupled to these sites by a hydrosilylation reaction.

The linkers or active centers may preferably be bound to the functionalities under consideration in the polymer under hydrosilylation conditions (review of the hydrosilylation reaction by Ojima in The Chemistry of Organic Silicon Compounds, 1989 John Wiley & Sons Ltd., 1480–1526). Suitable polysiloxanes modified in this manner are known from the literature ("Siloxane polymers and copolymers" White et al., in S. Patai (ed.), "The Chemistry of Organic Silicon Compounds", Wiley, Chichester, 1989, 46, 2954; C. Wandrey et al. TH:Asymmetry 1997, 8, 1975, the relevant contents of each of which are hereby incorporated by reference).

Preferably, the active center is bound to the linker or the molecular weight-enlarging polymer with one or more of the open bonds of polymer linkages in the compounds in the table.

Combining Linker with Active Center:

The details relating to joining the polymer to the linker/active center also apply synonymously to binding the active center to the linker.

The linker may preferably be bound to the active centers via heteroatoms or certain functionalities, such as C=O, $CH_2$, O, N, S, P, Si, B, wherein preferably ether/thioether bonds, amine bonds, amide bonds are linked or esterification, alkylation, silylation and addition reactions are performed on double bonds.

The following structures are especially preferred, wherein the indices x, y, z are freely selectable, but are preferably in the range 1–200 for x, 1–30 for y and 1–30 for z (scheme 1), which ranges include all values and subranges therebetween, including 3, 5, 7, 9, 12, 25, 32, 35, 41, 50, 65, 70, 72, 81, 90, 99, 105, 125, 145, 155, 185 and 190 for x; and 3, 4, 5, 7, 9, 12, 15, 18, 22, 24, 25 and 28, independently, for y and z.

Scheme 1

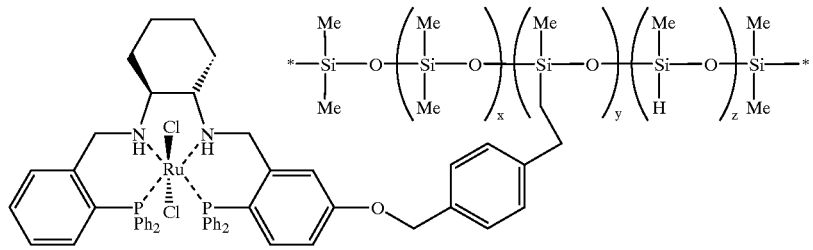

In the case of polyethers, the existing terminal OH group is suitable for binding to the linkers/active centers by ester or ether formation or by oxidation of this group to form an acid group with subsequent esterification or amide formation (Nagel et al., Chem. Ber. 1986, 119, 3326–3343; Nagel et al., Topics in Catalysis, 1998, 5, 3–23, the relevant contents of each of which are hereby incorporated by reference).

In the case of polyacrylates, an acid group or ester group is in each case present in the monomer constituent, to which Another preferable embodiment of the invention relates to the use of the products hydrogenated according to the invention in processes for the production of organic compounds.

An especially preferable embodiment of the invention provides molecular weight-enlarged ligands that include homochiral active centers of di-1,3-aminophosphines, wherein these centers are bound via a linker selected from the group

| a) | —Si(R$_2$)— | |
|---|---|---|
| b) | —(SiR$_2$—O)$_n$— | n = 1–10000 |
| c) | —(CHR—CHR—O)$_n$— | n = 1–10000 |
| d) | —(X)$_n$— | n = 1–20 |
| e) | Z—(X)$_n$— | n = 0–20 |
| f) | —(X)$_n$—W | n = 0–20 |
| g) | Z—(X)$_n$—W | n = 0–20 | wherein

R means H, ($C_1$–$C_8$) alkyl, ($C_6$–$C_{18}$) aryl, ($C_7$–$C_{19}$) aralkyl, (($C_1$–$C_8$) alkyl)$_{1-3}$—($C_6$–$C_{18}$)aryl, X means ($C_6$–$C_{18}$) arylene, ($C_1$–$C_8$) alkylene, ($C_1$–$C_8$) alkenylene, (($C_{1-8}$) alkyl)$_{1-3}$—($C_6$–$C_{18}$) arylene, ($C_7$–$C_{19}$) aralkylene, Z means on the polymer side C(=O)O—, C(=O)NH—, C(=O)—, NR, O, CHR, CH$_2$, C=S, S, PR, W means on the ligand side C(=O)O—, C(=O)NH—, C(=O)—, NR, O, CHR, CH$_2$, C=S, S, PR, or directly to the molecular weight-enlarging polymer.

The details relating to the molecular weight enlargement stated at the beginning in the process section apply here too.

A ligand is preferably used which includes an N,N'-bis (2-diphenylphosphanylbenzyl)cyclohexyl-1,2-diamine unit as the active center.

The ligand may preferably be produced by (a) binding the catalytically active center with a bound linker or directly to a monomer and polymerizing the latter in the presence of unmodified monomers, (b) binding the catalytically active center via a linker or directly to the finished polymer or (c) preparing polymers according to a) or b) and copolymerizing them with other polymers which may include catalytically active centers.

The ligands according to the invention are preferably used in the process according to the invention. The use thereof in connection with the transfer hydrogenation method in the process according to the invention is particularly advantageous.

Another especially preferable embodiment of the invention relates to catalysts specifically for use in the process according to the invention, which are synthesized from the ligands according to the invention that include an N,N'-bis (2-diphenylphosphanylbenzyl)-cyclohexyl-1,2-diamine unit and metals or metal ions selected from the group Ru, Rh, Ir, Pd, Ni, Pt, Co.

For the purposes of the invention, a membrane reactor preferably means any reaction vessel in which the molecular weight-enlarged catalyst is enclosed in a reactor, while low molecular weight substances are supplied to the reactor or are able to leave it. The membrane may be incorporated directly into the reaction chamber or be installed outside the chamber in a separate filtration module, in which the reaction solution flows continuously or intermittently through the filtration module and the retentate is returned to the reactor. Especially preferable embodiments are described, inter alia, in WO98/22415 and in Wandrey et al. in Jahrbuch 1998, Verfahrenstechnik und Chemieingenieurwesen, VDI pp. 151 et seq.; Wandrey et al. in Applied Homogeneous Catalysis with Organometallic Compounds, Vol. 2, VCH 1996, pp. 832 et seq.; Kragl et al., Angew. Chem. 1996, 6, 684 et seq., the relevant contents of each of which are hereby incorporated by reference.

For the purposes of the invention, a molecular weight-enlarged ligand/catalyst preferably means a ligand/catalyst in which the molecular weight-enlarging polymer is covalently bonded to the active center.

($C_1$–$C_8$) alkyl preferably means methyl, ethyl, n-propyl, isopropyl, n-butyl, isobutyl, sec-butyl, tert-butyl, pentyl, hexyl, heptyl or octyl, including all bond isomers.

A ($C_6$–$C_{18}$) aryl residue preferably means an aromatic residue having 6 to 18 C atoms. These in particular include compounds such as phenyl, naphthyl, anthryl, phenanthryl, biphenyl residues. These may be mono- or polysubstituted with ($C_1$–$C_8$) alkoxy, ($C_1$–$C_8$) haloalkyl, OH, Cl, NH$_2$, NO$_2$. It may also contain one or more heteroatoms such as N, S, O.

($C_1$–$C_8$) alkoxy is preferably a ($C_1$–$C_8$) alkyl residue, which is bound via an oxygen atom to the molecule concerned.

($C_1$–$C_8$) haloalkyl is preferably a ($C_1$–$C_8$) alkyl residue substituted with one or more halogen atoms. Chlorine and fluorine may in particular be considered as halogen atoms.

A ($C_7$–$C_{19}$) aralkyl residue is preferably a ($C_6$–$C_{18}$) aryl residue bound to the molecule via a ($C_1$–$C_8$) alkyl residue.

For the purposes of the invention, the term acrylate is also taken to mean methacrylate.

The chemical structures shown relate to all possible stereoisomers which may be obtained by modifying the configuration of the individual chiral centers, axes or planes, i.e. any possible diastereomers, as well as any optical isomers (enantiomers) included therein.

Preferably, for the purposes of the invention, a continuous reaction is also taken to mean the repeated fed batch process (batch UF). In this process, everything but the polymer is emptied out of the reactor, the solution is pressed through the membrane. The molecular weight-enlarged catalyst remains in the reactor and reacts with the newly added substrate and the catalysis cycle starts from the beginning.

EXAMPLES

Having generally described this invention, a further understanding can be obtained by reference to certain specific examples which are provided herein for purposes of illustration only and are not intended to be limiting unless otherwise specified.

Tetrahydrosalens:

Preparation of 2-diphenylphosphanylbenzaldehyde:

After 5.9 ml of triethylamine (43 mmol) and 334 mg of tetrakis(triphenylphosphine)palladium have been added, 5 ml of 2-bromobenzaldehyde (43 mmol) and 11.15 ml of diphenylphosphine (64.5 mmol) are refluxed in 150 ml of absolute toluene under a protective gas atmosphere in a three-necked flask equipped with a reflux condenser. Triethylamine hydrobromide precipitates as a white solid over the course of the reaction. After 12 hours, the reaction solution is filtered, washed three times with saturated ammonium hydrochloride solution and saturated sodium chloride solution and the solvent is removed in a rotary evaporator. The resultant crude product is recrystallised from methanol. Yield 10.61 g (85% of theoretical).

Preparation of (1 R,2R)-N-(2-diphenylphosphanylbenzyl) cyclohexane-1,2-diamine:

A solution, heated to 45° C., of 2.5 g of 2-diphenylphosphanylbenzaldehyde (8.6 mmol) in 250 ml of absolute ethanol is added dropwise over a period of 16 hours to a solution of 3.3 g of (1R,2R)-cyclohexane-1,2-diamine (28 mmol) in 500 ml of absolute ethanol at 0° C. under a protective gas atmosphere. The reaction solution is stirred for one hour at 0° C. and 1.37 g of sodium hydridoborate (36 mmol) are then added. The reaction mixture is slowly allowed to rise to room temperature and stirred for a further 12 hours. The reaction is then quenched by adding 100 ml of acetone and the solvent is completely removed in a rotary evaporator. The resultant residue is completely dissolved by adding 100 ml of saturated ammonium hydrochloride solution and 100 ml of methylene chloride. The organic phase is then separated and washed three times with water. 100 ml of 10% hydrochloric acid are then poured on and the mixture shaken. After a short time in the refrigerator, the product crystallises out as a white mass (hydrochloride). After drying under a high vacuum, a yield of 2.54 g (70% of theoretical) is obtained.

Preparation of 2-bromo-5-hydroxybenzaldehyde:

A solution of 4.2 ml of bromine (82 mmol) in 30 ml of chloroform is slowly added to a solution of 10 g of 3-hydroxybenzaldehyde (82 mmol) in 100 ml of chloroform. The reaction solution is then combined with 50 ml of 6% sodium carbonate solution and vigorously stirred. Once neutralisation is complete, the phases are separated and the solvent removed from the organic phase. The crude product is recrystallised with dilute acetic acid, whereupon 8.24 g of the product (7) are obtained as white needles at a yield of 50%. The yield may be raised to 65% by working up the residue in the mother liquor by column chromatography (mixture of 2-bromo-5-hydroxybenzaldehyde and 4-bromo-5-hydroxybenzaldehyde).

Preparation of 2-bromo-5-(tert.-butyldimethylsilanyloxy) benzaldehyde:

A solution of 10 g of 2-bromo-5-hydroxybenzaldehyde (49 mmol), 8.9 g of tert.-butyldimethylsilyl chloride (59.6 mmol) and 8.11 g of imidazole in 20 ml of dimethylformamide is stirred for 1 hour at room temperature under a protective gas atmosphere. The reaction solution is then combined with 100 ml of saturated ammonium hydrochloride solution and stirred for 15 minutes. The crude solution is extracted twice with 100 ml of methylene chloride. The combined organic phases are then washed three times with water and once with saturated sodium chloride solution and then dried with magnesium sulfate. After removal of the solvent in a rotary evaporator and subsequent drying under a high vacuum, 14.98 g of the chromatographically purified product are obtained at a yield of 97%.

Preparation of 5-(tert.-butyldimethylsilanyloxy-2-diphenylphosphanylbenzaldehyde:

After 8.7 ml of triethylamine (62 mmol) and 334 mg of tetrakis(triphenylphosphine)palladium (0.28 mmol) have been added, 15.15 g of 2-bromo-5-tert.-butyldimethylsilanyloxy) benzaldehyde (48 mmol) and 10.8 ml of diphenylphosphine (62 mmol) are refluxed in 150 ml of absolute toluene under a protective gas atmosphere in a three-necked flask equipped with a reflux condenser. Triethylamine hydrobromide precipitates as a white solid over the course of the reaction. After 12 hours, the reaction solution is filtered, washed three times with saturated ammonium hydrochloride solution and once with water. The product is then dried with magnesium sulfate, the solvent removed in a rotary evaporator and drying performed under a high vacuum. According to GC-MS, the product is 97% pure and may be used directly for the following reactions. Yield 16.14 g (80% of theoretical).

Preparation of 2-diphenylphosphanyl-5-hydroxybenzaldehyde:

A solution of 11.61 g of 5-(tert.-butyldimethylsilanyloxy)-2-diphenylphosphanylbenzaldehyde (28 mmol), 3.2 g of potassium fluoride (55 mmol) and 1.29 ml of 48% hydrobromic acid (7 mmol) in 150 ml of dimethylformamide is stirred for 1 hour at room temperature under a protective gas atmosphere. The reaction solution is then combined with 100 ml of saturated ammonium hydrochloride solution and extracted twice with methylene chloride. The organic phase is washed three times with water and once with saturated sodium chloride solution and then dried with magnesium sulfate. After removal of the solvent in a rotary evaporator and subsequent drying under a high vacuum, the resultant product (8.15 g, corresponding to 95% yield) may be used directly for the subsequent reaction.

Preparation of 2-diphenylphosphanyl-5-(4-vinylbenzyloxy benzaldehyde:

7.3 g of 2-diphenylphosphanyl-5-hydroxybenzaldehyde (24 mmol) are combined with 2.41 g of sodium hydride (96 mmol) in 100 ml of dimethylformamide at room temperature under an inert gas atmosphere. Once evolution of hydrogen has subsided (approx. 1 hour), 528 mg of 2,6-di-tert.-butyl-p-cresol (2.4 mmol) as stabiliser and 3.53 ml of p-vinylbenzyl chloride (24 mmol) are slowly added. After 12 hours, the mixture is combined with 100 ml of saturated ammonium chloride solution and extracted twice with methylene chloride. The organic phase is washed three times with water and once with saturated sodium chloride solution. Drying is then performed with magnesium sulfate and the solvent removed. The crude product is purified by silica gel chromatography (12:1 isohexane/ethyl acetate). 5.67 g of the product are obtained as a yellow solid (yield 56%).

Preparation of (1R,2R)-N-(2-diphenylphosphanylbenzyl)-N-[2-diphenylphosphanyl-5-(4-vinylbenzyloxy)benzyl] cyclohexane-1,2-diamine:

2.54 g of (1R,2R)-N-(2-diphenylphosphanylbenzyl) cyclohexane-1,2-diamine hydrochloride (6 mmol) are combined with 100 ml of methylene chloride and 100 ml of saturated sodium hydrogen carbonate solution. Once the phases have separated, the aqueous phase is extracted twice more with methylene chloride and the combined organic phases are washed with saturated sodium chloride solution. Drying is then performed with magnesium sulfate and the solvent removed in a rotary evaporator. After drying under a high vacuum, 1.71 g of (1R,2R)-N-(2-diphenylphosphanylbenzyl)cyclohexane-1,2-diamine (4.4 mmol) are obtained as an air-sensitive clear oil. This is dissolved in 250 ml of absolute ethanol under a protective gas atmosphere in a three-necked flask equipped with a reflux condenser. Once combined with 1.85 g of 2-diphenylphosphanyl-5-(4-vinylbenzyloxy)benzaldehyde (4.4 mmol) and 96 mg of 2,6-di-tert.-butyl-p-cresol (0.4 mmol), the reaction solution is refluxed for 1 hour under protective gas. The reaction mixture is then left to cool and combined with 1.66 g (44 mmol) of sodium hydridoborate. After 3 hours, the reaction is quenched by adding 50 ml of acetone and the solvent is completely removed in a rotary evaporator. The resultant residue is stirred with 100 ml of saturated ammonium hydrochloride solution and 100 ml of methylene chloride until completely dissolved. The aqueous phase is extracted twice more with methylene chloride and the combined organic phases are washed with water and saturated sodium chloride solution. Drying is then performed with magnesium sulfate and the solvent removed. After drying under a high vacuum, 2.83 g of the product, corresponding to a yield of 79%, are obtained as a white mass (stabiliser content according to NMR 9.4%).

Preparation of ruthenium dichloride (1R,2R)-N-(2-diphenylphosphanylbenzyl)-N'-[2-diphenylphosphanyl-5-(4-vinylbenzyloxy)benzyl]cyclohexane-1,2-diamine:

2.83 g of (1R,2R)-N-(2-diphenylphosphanylbenzyl)-N'-[2-diphenylphosphanyl-5-(4-vinylbenzyloxy)benzyl] cyclohexan-1,2-diamine (3.5 mmol, 9.4% stabiliser) are refluxed for 1 hour under protective gas with 3.36 g of dichlorotetrakis(dimethyl sulfoxide)ruthenium(II) (7 mmol) in 200 ml of absolute toluene. During the reaction, 120 mg of a yellowish solid precipitate out, which can be identified as a ruthenium-stabiliser complex. Once the reaction solution has been filtered, the solvent is removed in a rotary evaporator and the product separated by column chromatography on silica gel (isohexane/ethyl acetate 2:1). In order to isolate the product, the chromatographic fractions should not be evaporated to dryness, but instead combined with isohexane once the eluent has largely been removed. As a result, the product precipitates as a yellow/orange powder at a yield of 1.86 g (55%).

Polymer Linkage of the Catalyst:

299 mg of the linkable catalyst (0.31 mmol) are dissolved in 25 ml of absolute toluene with 1 g of polysiloxane polymer (molecular weight approx. 11700 g/mol, 0.08 mmol, functionalization 19%). The reaction mixture is then degassed (freeze/pump/thaw method), combined with 10 µl of platinum divinyltetramethyldisiloxane catalyst and stirred for 1 hour at 50° C. The course of the reaction may be monitored by NMR spectroscopy (disappearance of vinyl proton signals at 5.2 and 5.7 ppm). The remaining hydridosiloxane units are then converted by being combined with 1 g of vinyl tris(2-methoxyethoxy)silane (3.5 mmol) and stirred overnight at 50° C. The functionalized polymer is then purified by means of nanofiltration (MPF-50 membrane, Celfa, solvent methylene chloride, 10 ml reactor, 20 residence times). After removal of the solvent in a rotary evaporator and drying under a high vacuum, 1.45 g of the polymer-bound catalyst are obtained.

Influence of Base Concentration on Catalytic Activity and Enantiomeric Excess:

In order to investigate the influence of different isopropylate concentrations on catalytic activity and enantiomeric excess, activity measurements were performed at differing isopropylate concentrations (as described above). This investigation was performed by varying the base concentration for catalyst activation in the range from 0.125 mM to 4 mM. Acetophenone concentration was 250 mM and catalyst concentration 0.5 mM. The batches were performed on a 20 ml scale at 45° C. with an incubation time of 45 minutes. As the result, it may be stated (FIG. 3), that higher base concentrations bring about greater catalyst activation (increasing turn-over frequency under initial reaction rate conditions, tof$_{init}$). It is simultaneously found that the course of the enantiomeric excess curve becomes more unfavourable over the course of the batch experiment at higher base concentrations (FIG. 4).

Performance of Continuous Reaction in the Membrane Reactor:

The continuous experiments are performed in a membrane reactor (10 and 3 ml reactor), adjusted to a temperature of 45° C., using an Amicon YC 05 nanofiltration membrane. Absolute, degassed isopropanol was used as the solvent and hydrogen donor.

At the beginning of the first test (FIG. 5), 146 mg of the polymer-bound catalyst (functionalization 0.308 mmol/g, preparation as above) were dissolved in 10 ml of absolute isopropanol and flushed into the membrane reactor (reactor volume 10 ml). Five equivalents of base were then apportioned in the form of a 0.1 M isopropanolic potassium isopropylate solution. The substrate acetophenone was then continuously introduced into the reactor as a 24 mM solution. The catalyst concentration relative to the substrate was 28 mol % at this point. The solvent flow rate was adjusted such that the residence time of the substrate in the reactor was one hour.

The second test (FIG. 6) proceeded under conditions comparable to those of the first. Unlike the first test, however, only one equivalent of base relative to the catalyst was initially apportioned. A minimal quantity of base was additionally constantly apportioned during the reaction. The base concentration was adjusted in such a manner as to replace the quantity of base lost due to moisture or flushing out (0.05 mM/residence time). The intended residence time of the substrate was again 1 hour. However, due to inaccuracies in the pumping rate, variations occurred in the residence time, for which reason FIG. 6 states the true residence time which describes the reactor volume actually exchanged.

This application is based on German patent application DE 100 02 975.2, filed Jan. 24, 2000, the entire contents of which are hereby incorporated by reference.

Having now fully described the invention, it will be apparent to one of ordinary skill in the art that many changes and modifications can be made thereto without departing from the spirit or scope of the invention as set forth herein.

What is claimed is:

1. A process, comprising:

in a continuous process in a membrane reactor, asymmetrically hydrogenating at least one C=C, C=N or C=O double bond in a substrate molecule in the presence of H$_2$ gas or by transfer hydrogenation and a molecular weight-enlarged catalyst comprising an active hydrogenation moiety bonded to a polymer in the absence of a mediator that facilitates hydrogenation of one of said double bond types.

2. The process according to claim 1, wherein the hydrogenation comprises an asymmetric transfer of hydrogen to said double bond by said catalyst.

3. The process according to claim 1, wherein said double bond is comprised within a substrate.

4. The process according to claim 1, wherein said continuous process is carried out in either dead end or crossflow filtration mode.

5. The process according to claim 1, wherein the hydrogenation is carried out at a pressure of 0.1–100 Mpa.

6. The process according to claim 5, wherein the hydrogenation is carried out at a pressure of 0.2–0.5 Mpa.

7. The process according to claim 1, wherein said catalyst comprises a molecular weight-enlarging polymer selected from the group consisting of polyacrylates, polyvinylpyrrolidones, polysiloxanes, polybutadienes, polyisoprenes, polyalkanes, polystyrenes, polyoxazolines, polyethers and mixtures thereof.

8. The process according to claim 1, wherein said catalyst has an average molecular weight in the range of 1,000–1,000,000 g/mol.

9. The process according to claim 8, wherein said catalyst has an average molecular weight in the range of 5,000–300,000 g/mol.

10. The process according to claim 1, wherein said catalyst comprises:

at least one active center which functions catalytically in asymmetric catalytic hydrogenation;

optionally, a linker; and a molecular weight-enlarging polymer, wherein said active center is bound to said molecular weight-enlarging polymer through said linker or is bound directly to said molecular weight-enlarging polymer;

wherein said linker is a member selected from the group consisting of formulae a)–g):

| | | |
|---|---|---|
| a) | —Si(R₂)— | |
| b) | —(SiR₂—O)ₙ— | n = 1–10000; |
| c) | —(CHR—CHR—O)ₙ— | n = 1–10000; |
| d) | —(X)ₙ— | n = 1–20; |
| e) | Z—(X)ₙ— | n = 0–20; |
| f) | —(X)ₙ—W | n = 0–20; and |
| g) | Z—(X)ₙ—W | n = 0–20; | wherein R is H, ($C_1$–$C_8$) alkyl, ($C_6$–$C_{18}$) aryl, ($C_7$–$C_{19}$) aralkyl, or (($C_1$–$C_8$) alkyl)$_{1-3}$—($C_6$–$C_{18}$) aryl;

X is ($C_6$–$C_{18}$) arylene, ($C_1$–$C_8$) alkylene, ($C_1$–$C_8$) alkenylene, (($C_1$–$C_8$) alkyl)$_{1-3}$—($C_6$–$C_{18}$) arylene, or ($C_7$–$C_{19}$) aralkylene;

Z is C(=O)O—, C(=O)NH—, C(=O)—, NR, O, CHR, CH₂, C=S, S, or PR, Z being bound directly to said molecular weight-enlarging polymer; and W is C(=O)O—, C(=O)NH—, C(=O)—, NR, O, CHR, CH₂, C=S, S, or PR, W being bound directly to said active center.

11. The process according to claim 8, wherein said catalyst has an average molecular weight of at least 1,000 g/mol.

12. The process according to claim 1, wherein said catalyst comprises at least one active center selected from the group consisting of compounds having the formulas in the following table, and combinations thereof:

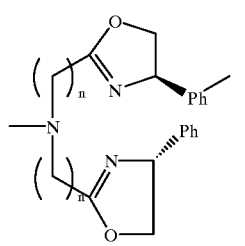

n = 0–5

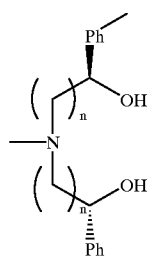

n = 0–5

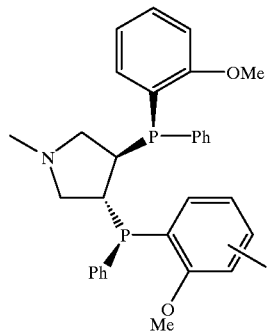

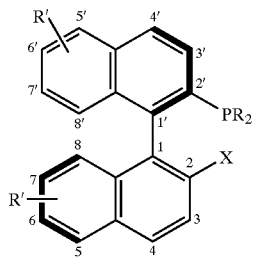

R = cyclohexyl, ($C_6$–$C_{18}$) aryl
R' = H, polymer linkage
X = PR₂, Ome

-continued
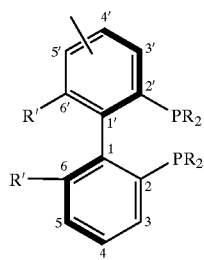
R = cyclohexyl, (C$_6$–C$_{18}$) aryl
R' = CH$_3$, OMe, CF$_3$, H, tert.$^+$Bu
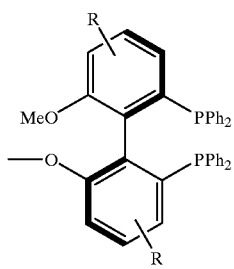
R = H, CF$_3$, OMe, CH$_3$
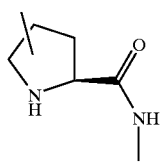
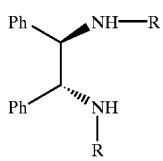
R = H, (C$_1$–C$_8$) alkyl or polymer linkage
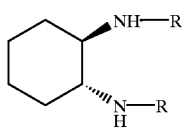
R = H, (C$_1$–C$_8$) alkyl or polymer linkage
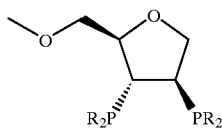
R = cyclohexyl, (C$_6$–C$_{18}$) aryl
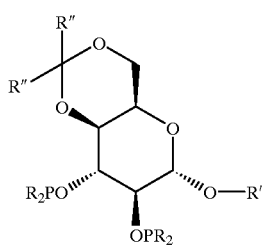
R = cyclohexyl, (C$_6$–C$_{18}$) aryl
R' = (C$_1$–C$_8$) alkyl, (C$_7$–C$_{19}$) aralkyl, (C$_6$–C$_{18}$) aryl, polymer linkage
R" = (C$_1$–C$_8$) alkyl or polymer linkage
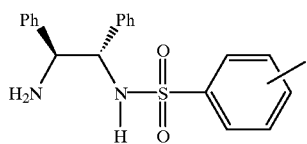

-continued
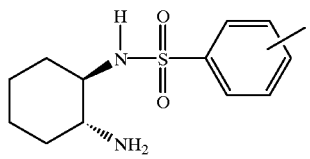
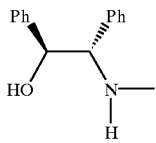
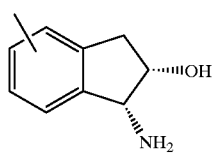
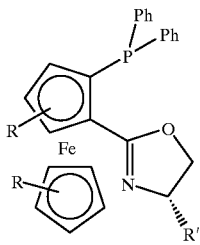
R' = H, polymer linkage
R' = (C$_1$–C$_8$) alkyl,
(C$_7$–C$_{19}$) aralkyl, (C$_6$–C$_{18}$) aryl
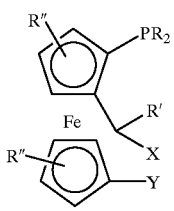
R = cyclohexyl, (C$_6$–C$_{18}$) aryl
R' = (C$_1$–C$_8$) alkyl, H, polymer linkage
R' = H, polymer linkage
X = NR'$_2$, NR'H, OMe, Oac
Y = PR$_2$, H
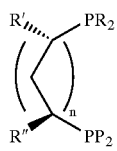
R = cyclohexyl, (C$_6$–C$_{18}$) aryl
R' = (C$_1$–C$_8$) alkyl, (C$_6$–C$_{18}$) aryl, H
R" = polymer linkage
n = 0, 1, 2
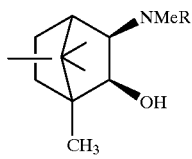
R = H, (C$_1$–C$_8$) alkyl, polymer linkage
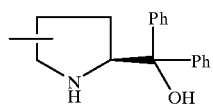
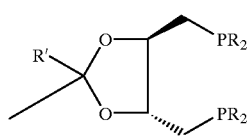
R = cyclohexyl, (C$_6$–C$_{18}$) aryl
R' = H, (C$_1$–C$_8$) alkyl, (C$_6$–C$_{18}$) aryl -continued

R = (C$_1$–C$_8$) alkyl
R' = H, (C$_1$–C$_8$) alkyl,
O—(C$_7$–C$_{19}$) aralkyl,
O—(C$_6$–C$_{18}$) aryl, OH

R = cyclohexyl, (C$_6$–C$_{18}$) aryl
R' = H, polymer linkage

R = cyclohexyl, (C$_6$–C$_{18}$) aryl
R' = H, polymer linkage

R = H, (C$_1$–C$_8$) alkyl,
(C$_7$–C$_{19}$) aralkyl, polymer linkage

R = cyclohexyl, (C$_6$–C$_{18}$) aryl
R' = H, (C$_1$–C$_8$) alkyl, polymer linkage
R" = H, (C$_1$–C$_8$) alkyl, (C$_7$–C$_{19}$) aralkyl,
(C$_6$–C$_{18}$) aryl, polymer linkage

R = cyclohexyl, (C$_6$–C$_{18}$) aryl
R' = H, (C$_1$–C$_8$) alkyl, (C$_7$–C$_{19}$) aralkyl,
(C$_6$–C$_{18}$) aryl, polymer linkage

R = cyclohexyl, (C$_6$–C$_{18}$) aryl
X = CH$_2$, O, S, PR

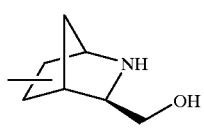

-continued
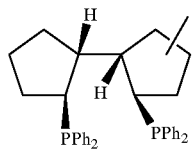
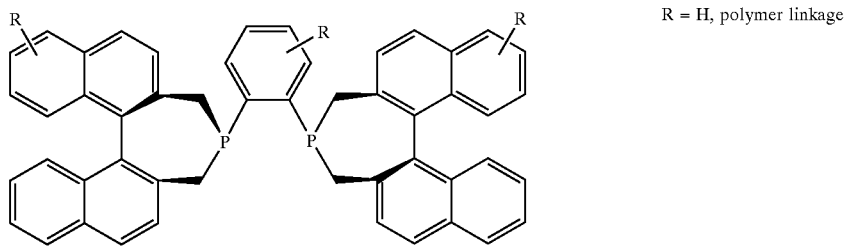
R = H, polymer linkage
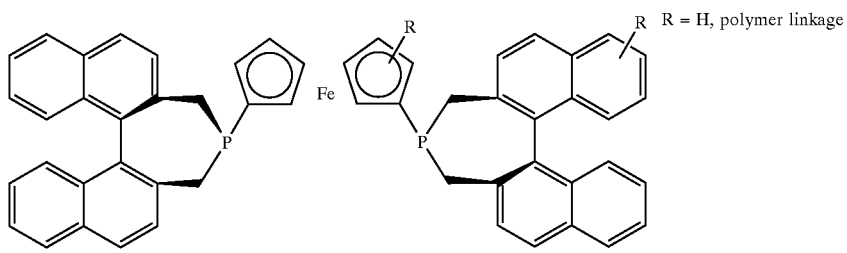
R = H, polymer linkage
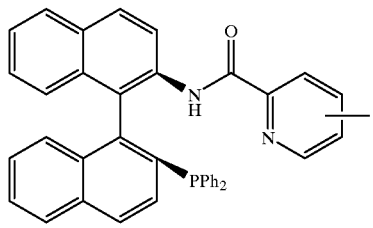
(n = 1–6)
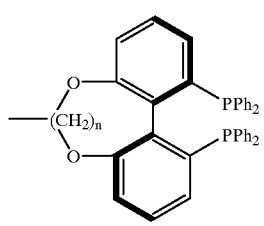
R = ($C_1$–$C_8$) alkyl, ($C_7$–$C_{19}$) aralkyl, ($C_6$–$C_{18}$) aryl, polymer linkage
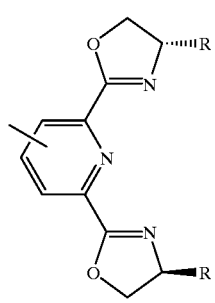

-continued
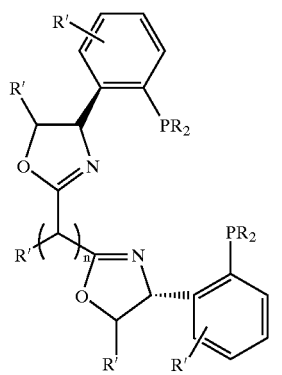
R = cyclohexyl, (C$_6$–C$_{18}$) aryl
R' = H, (C$_1$–C$_8$) alkyl, (C$_7$–C$_{19}$) aralkyl, (C$_6$–C$_{18}$) aryl, polymer linkage
N = 0–5
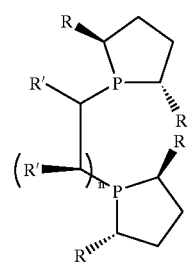
N = 0,1
R = (C$_1$–C$_8$) alkyl, H
R' = H, (C$_1$–C$_8$) alkyl, (C$_7$–C$_{19}$) aralkyl, (C$_6$–C$_{18}$) aryl, polymer linkage
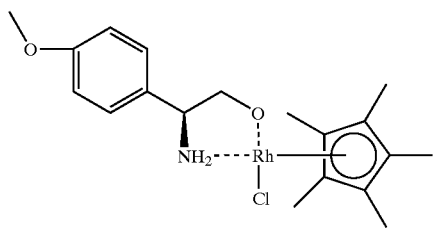
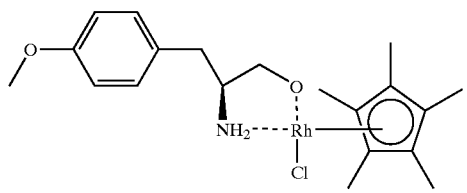
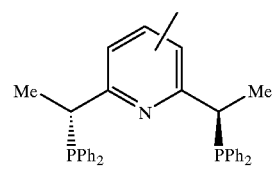
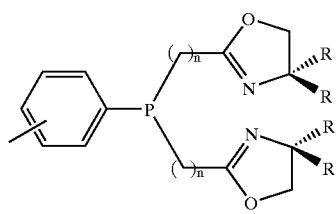
R = (C$_1$–C$_8$) alkyl, (C$_6$–C$_{18}$) aryl,
n = 0–5

-continued

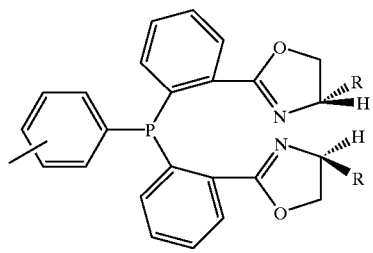

R = (C₁–C₈) alkyl,
(C₇–C₁₉) aralkyl, (C₆–C₁₈) aryl

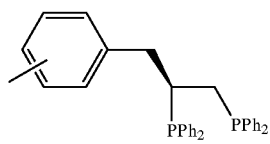

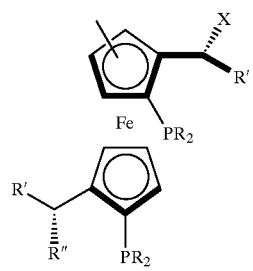

R = cyclohexyl, (C₆–C₁₈) aryl
R' = (C₁–C₈) alkyl,
(C₆–C₁₈) aryl, polymer linkage
X = H, (C₁–C₈) alkyl, (C₇–C₁₉) aralkyl,
(C₆–C₁₈) aryl, polymer linkage,
OR", OAc, NR₂", NH₂,

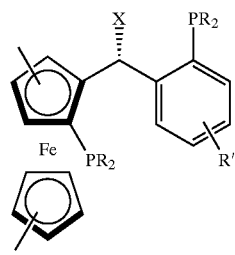

R = cyclohexyl, (C₆–C₁₈) aryl
R' = (C₁–C₈) alkyl,
(C₆–C₁₈) aryl polymer linkage
X = H, (C₁–C₈) alkyl,
(C₆–C₁₈) aryl, OR",
OAc, NR₂", NH₂, polymer linkage

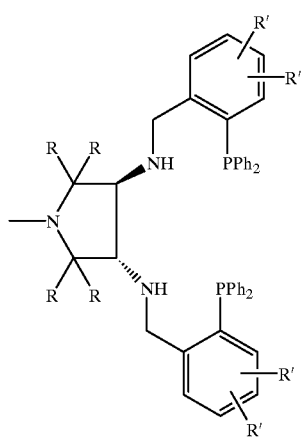

R = (C₁–C₈) alkyl, H
R' = H, (C₁–C₈) alkyl

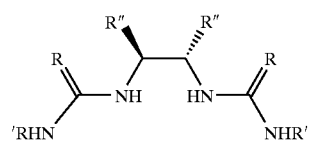

R = O, S, HH
R' = H, (C₁–C₈) alkyl, (C₇–C₁₉) aralkyl,
(C₆–C₁₈) aryl, polymer linkage
R" = (C₁–C₈) alkyl,
(C₇–C₁₉) aralkyl, (C₆–C₁₈) aryl -continued

| | |
|---|---|
| 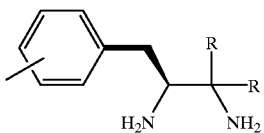 | R = (C₁–C₈) alkyl, (C₇–C₁₉) aralkyl, (C₆–C₁₈) aryl, |
| 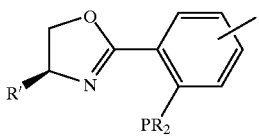 | R = (C₁–C₈) alkyl, (C₇–C₁₉) aralkyl, (C₆–C₁₈) aryl<br>R" = (C₁–C₈) alkyl, (C₇–C₁₉) aralkyl, (C₆–C₁₈) aryl |
| 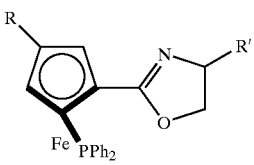 | R = polymer linkage, H<br>R' (C₁–C₈) alkyl, (C₇–C₁₉) aralkyl, (C₆–C₁₈) aryl polymer linkage |
| 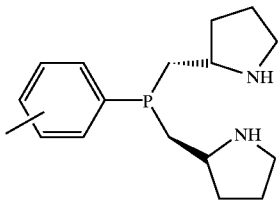 | |

13. The process according to claim 1, wherein said catalyst comprises one or more metals or metal ions selected from the group consisting of Ru, Rh, Ir, Pd, Ni, Pt, Co, ions thereof, and mixtures thereof.

14. The process according to claim 1, wherein said process produces a hydrogenated product, further comprising separating said hydrogenated product from said catalyst.

15. The process according to claim 1, wherein said catalyst comprises:
   at least one ligand comprising:
      an average molecular weight of at least 1000 g/mol;
      a molecular weight-enlarging polymer;
      optionally, a linker; and
      at least one active center;
   wherein said active center is bound to said molecular weight-enlarging polymer through said linker or is bound directly to said molecular weight-enlarging polymer; and
   wherein said active center is selected from the group consisting of compounds having the formulas in the following table, and combinations thereof:

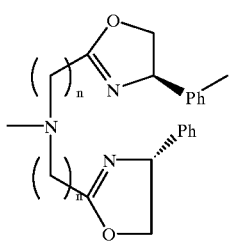

n = 0–5

-continued
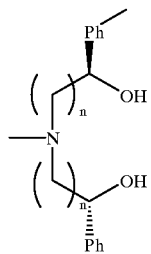
n = 0–5
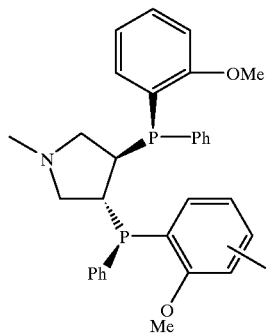
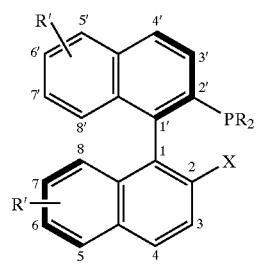
R = cyclohexyl, (C$_6$–C$_{18}$) aryl
R' = H, polymer linkage
X = PR$_2$, Ome
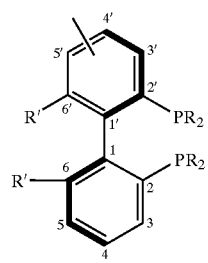
R = cyclohexyl, (C$_6$–C$_{18}$) aryl
R' = CH$_3$, OMe, CF$_3$, H, tert.Bu
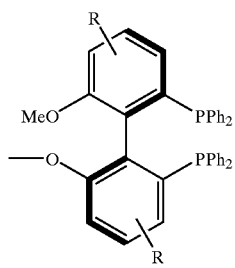
R = H, CF$_3$, OMe, CH$_3$
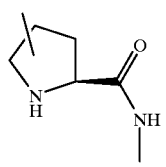

-continued
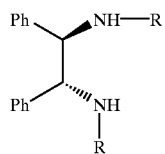
R = H, $(C_1-C_8)$ alkyl or polymer linkage
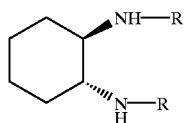
R = H, $(C_1-C_8)$ alkyl or polymer linkage
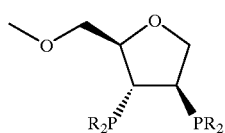
R = cyclohexyl, $(C_6-C_{18})$ aryl
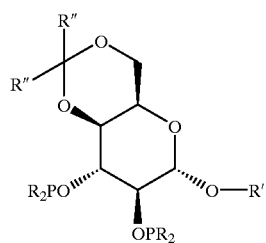
R = cyclohexyl, $(C_6-C_{18})$ aryl
R' = $(C_1-C_8)$ alkyl, $(C_7-C_{19})$ aralkyl, $(C_6-C_{18})$ aryl,l polymer linkage
R" = $(C_1-C_8)$ alkyl or polymer linkage
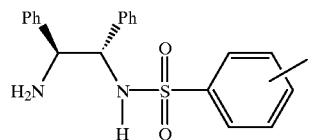
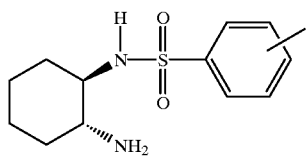
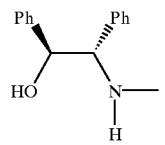
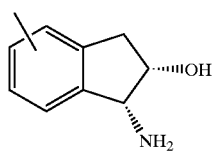

-continued

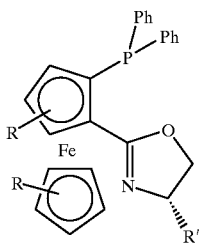

R' = H, polymer linkage
R" = (C$_1$–C$_8$) alkyl,
(C$_7$–C$_{19}$) aralkyl, (C$_6$–C$_{18}$) aryl

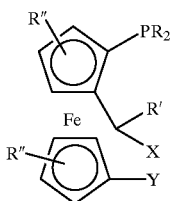

R = cyclohexyl, (C$_6$–C$_{18}$) aryl
R' = (C$_1$–C$_8$) alkyl, H, polymer linkage
R" = H, polymer linkage
X = NR'$_2$, NR'H, OMe, Oac
Y = PR$_2$, H

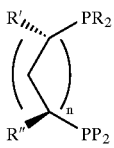

R = cyclohexyl, (C$_6$–C$_{18}$) aryl
R' = (C$_1$–C$_8$) alkyl, (C$_6$–C$_{18}$) aryl, H
R" = polymer linkage
N = 0, 1, 2

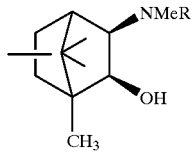

R = H, (C$_1$–C$_8$) alkyl, polymer linkage

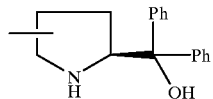

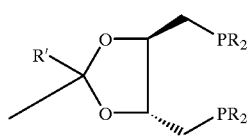

R = cyclohexyl, (C$_6$–C$_{18}$) aryl
R' = H, (C$_1$–C$_8$) alkyl, (C$_6$–C$_{18}$) aryl

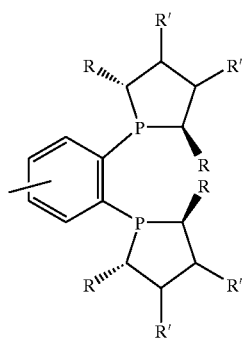

R = (C$_1$–C$_8$) alkyl
R' = H, (C$_1$–C$_8$) alkyl,
O—(C$_7$–C$_{19}$) aralkyl,
O—(C$_6$–C$_{18}$) aryl, OH

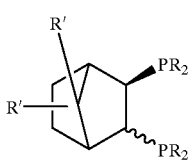

R = cyclohexyl, (C$_6$–C$_{18}$) aryl
R' = H, polymer linkage

-continued

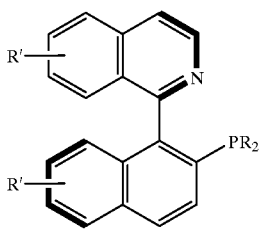

R = cyclohexyl, (C$_6$–C$_{18}$) aryl
R' = H, polymer linkage

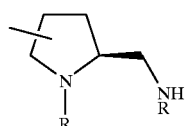

R = H, (C$_1$–C$_8$) alkyl,
(C$_7$–C$_{19}$) aralkyl, polymer linkage

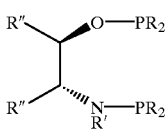

R = cyclohexyl, (C$_6$–C$_{18}$) aryl
R' = H, (C$_1$–C$_8$) alkyl, polymer linkage
R'' = H, (C$_1$–C$_8$) alkyl, (C$_7$–C$_{19}$) aralkyl,
(C$_6$–C$_{18}$) aryl, polymer linkage

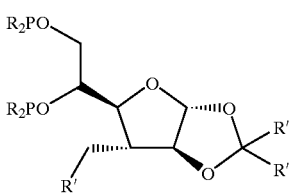

R = cyclohexyl, (C$_6$–C$_{18}$) aryl
R' = H, (C$_1$–C$_8$) alkyl, (C$_7$–C$_{19}$) aralkyl,
(C$_6$–C$_{18}$) aryl, polymer linkage

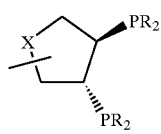

R = cyclohexyl, (C$_6$–C$_{18}$) aryl
X = CH$_2$, O, S, PR

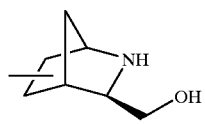

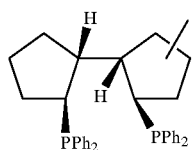

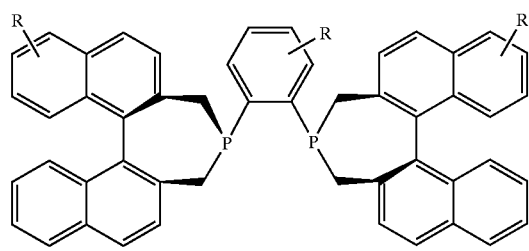

R = H, polymer linkage

-continued
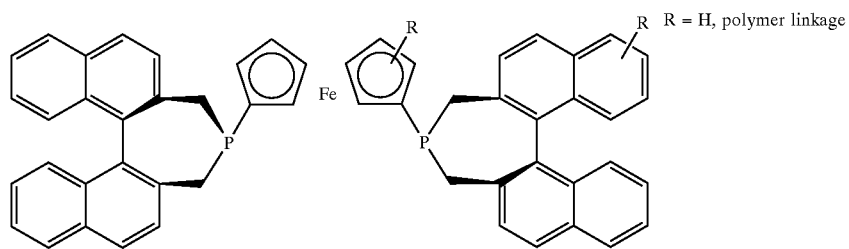
R = H, polymer linkage
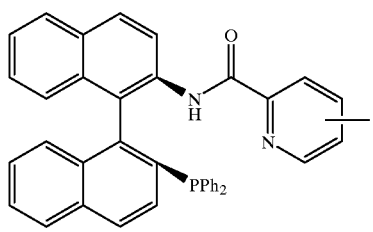
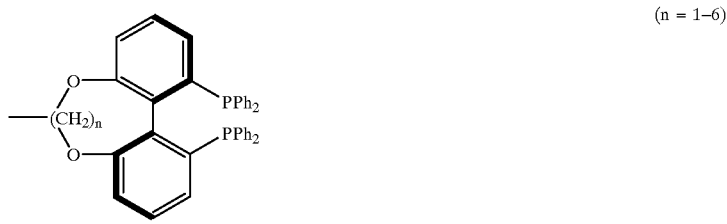
(n = 1–6)
R = (C$_1$–C$_8$) alkyl, (C$_7$–C$_{19}$) aralkyl, (C$_6$–C$_{18}$) aryl, polymer linkage
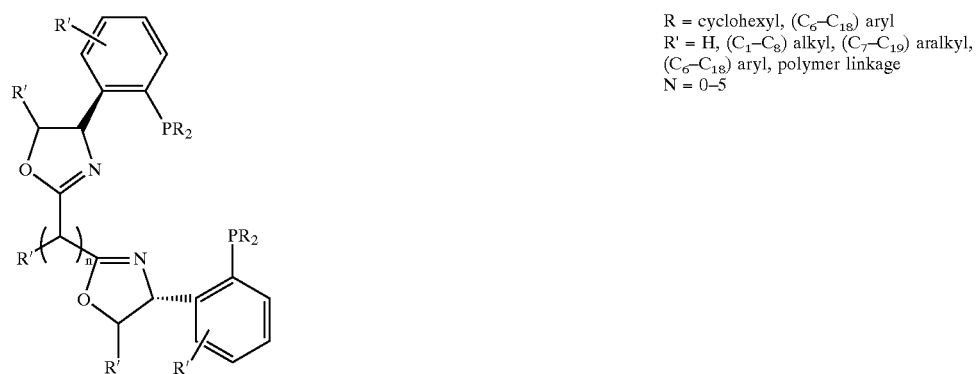
R = cyclohexyl, (C$_6$–C$_{18}$) aryl
R' = H, (C$_1$–C$_8$) alkyl, (C$_7$–C$_{19}$) aralkyl, (C$_6$–C$_{18}$) aryl, polymer linkage
N = 0–5

-continued
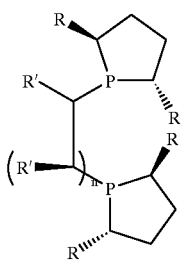
N = 0,1
R = $(C_1-C_8)$ alkyl, H
R' = H, $(C_1-C_8)$ alkyl,
$(C_7-C_{19})$ aralkyl,
$(C_6-C_{18})$ aryl, polymer linkage
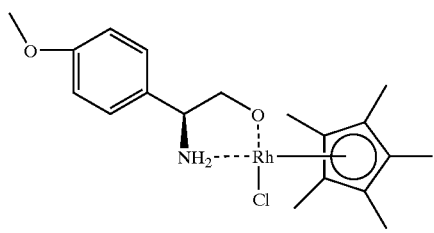
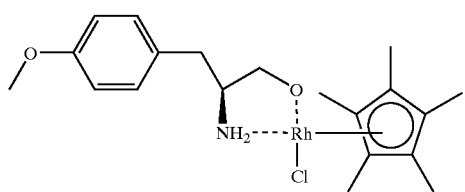
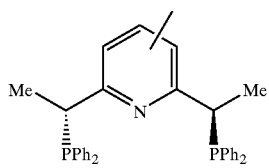
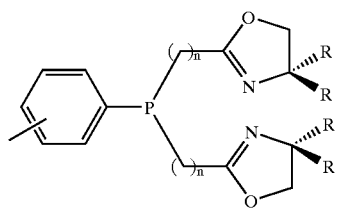
R = $(C_1-C_8)$ alkyl, $(C_6-C_{18})$ aryl,
n = 0–5
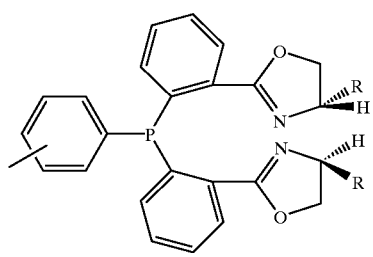
R = $(C_1-C_8)$ alkyl,
$(C_7-C_{19})$ aralkyl, $(C_6-C_{18})$ aryl
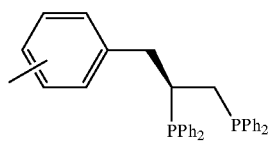

-continued

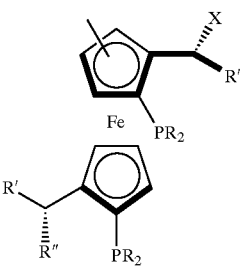

R = cyclohexyl, (C$_6$–C$_{18}$) aryl
R' = (C$_1$–C$_8$) alkyl, (C$_6$–C$_{18}$) aryl, polymer linkage
X = H, (C$_1$–C$_8$) alkyl, (C$_7$–C$_{19}$) aralkyl, (C$_6$–C$_{18}$) aryl, polymer linkage, OR", OAc, NR$_2$", NH$_2$,

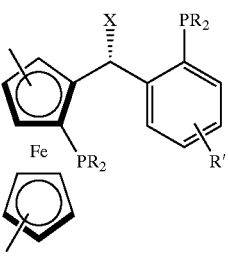

R = cyclohexyl, (C$_6$–C$_{18}$) aryl
R' = (C$_1$–C$_8$) alkyl, (C$_6$–C$_{18}$) aryl polymer linkage
X = H, (C$_1$–C$_8$) alkyl, (C$_6$–C$_{18}$) aryl, OR",
OAc, NR$_2$", NH$_2$, polymer linkage

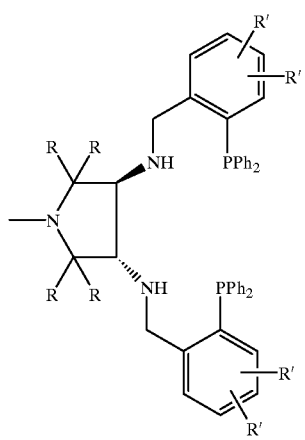

R = (C$_1$–C$_8$) alkyl, H
R' = H, (C$_1$–C$_8$) alkyl

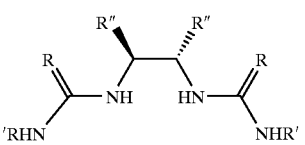

R = O, S, HH
R' = H, (C$_1$–C$_8$) alkyl, (C$_7$–C$_{19}$) aralkyl, (C$_6$–C$_{18}$) aryl, polymer linkage
R" = (C$_1$–C$_8$) alkyl, (C$_7$–C$_{19}$) aralkyl, (C$_6$–C$_{18}$) aryl

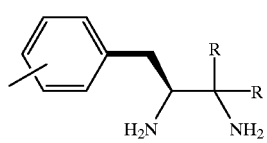

R = (C$_1$–C$_8$) alkyl, (C$_7$–C$_{19}$) aralkyl, (C$_6$–C$_{18}$) aryl,

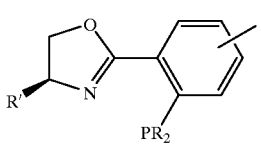

R = (C$_1$–C$_8$) alkyl, (C$_7$–C$_{19}$) aralkyl, (C$_6$–C$_{18}$) aryl
R" = (C$_1$–C$_8$) alkyl, (C$_7$–C$_{19}$) aralkyl, (C$_6$–C$_{18}$) aryl

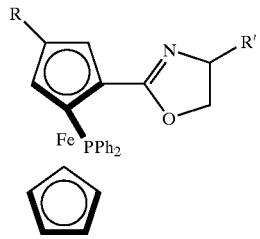

R = polymer linkage, H
R' ($C_1$–$C_8$) alkyl, ($C_7$–$C_{19}$) aralkyl, ($C_6$–$C_{18}$) aryl polymer linkage

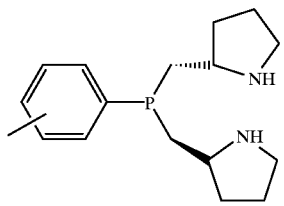

wherein said linker is a member selected from the group consisting of formulae a)–g):

| | | |
|---|---|---|
| a) | —Si($R_2$)— | |
| b) | —(Si$R_2$—O)$_n$— | n = 1–10000; |
| c) | —(CHR—CHR—O)$_n$— | n = 1–10000; |
| d) | —(X)$_n$— | n = 1–20; |
| e) | Z—(X)$_n$— | n = 0–20; |
| f) | —(X)$_n$—W | n = 0–20; and |
| g) | Z—(X)$_n$—W | n = 0–20; | wherein R is H, ($C_1$–$C_8$) alkyl, ($C_6$–$C_{18}$) aryl, ($C_7$–$C_{19}$) aralkyl, or (($C_1$–$C_8$) alkyl)$_{1-3}$—($C_6$–$C_{18}$) aryl;

X is ($C_6$–$C_{18}$) arylene, ($C_1$–$C_8$) alkylene, ($C_1$–$C_8$) alkenylene, (($C_1$–$C_8$) alkyl)$_{1-3}$—($C_6$–$C_{18}$) arylene, or ($C_7$–$C_{19}$) aralkylene;

Z is C(=O)O—, C(=O)NH—, C(=O)—, NR, O, CHR, $CH_2$, C=S, S, or PR, Z being bound directly to said molecular weight-enlarging polymer; and W is C(=O)O—, C(=O)NH—, C(=O)—, NR, O, CHR, $CH_2$, C=S, S, or PR, W being bound directly to said active center.

16. The process according to claim 15, wherein said active center is bound to said linker or said molecular weight-enlarging polymer with one or more of the open bonds or polymer linkages in the compounds in said table.

* * * * *